US010578623B2

(12) United States Patent
Woodbury et al.

(10) Patent No.: US 10,578,623 B2
(45) Date of Patent: *Mar. 3, 2020

(54) PEPTIDE ARRAY QUALITY CONTROL

(71) Applicant: Arizona Board of Regents on behalf of Arizona State University, Scottsdale, AZ (US)

(72) Inventors: Neal Woodbury, Tempe, AZ (US); Stephen Johnston, Tempe, AZ (US); Phillip Stafford, Phoenix, AZ (US)

(73) Assignee: ARIZONA BOARD OF REGENTS OF BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/991,892

(22) Filed: May 29, 2018

(65) Prior Publication Data

US 2018/0275136 A1    Sep. 27, 2018

Related U.S. Application Data

(63) Continuation of application No. 14/773,750, filed as application No. PCT/US2014/029822 on Mar. 14, 2014, now Pat. No. 10,006,919.

(60) Provisional application No. 61/799,494, filed on Mar. 15, 2013.

(51) Int. Cl.
G01N 33/68 (2006.01)

(52) U.S. Cl.
CPC .................. G01N 33/6845 (2013.01)

(58) Field of Classification Search
None
See application file for complete search history.

(56) References Cited

U.S. PATENT DOCUMENTS

| | | | |
|---|---|---|---|
| 5,143,854 | A | 9/1992 | Pirrung et al. |
| 5,571,639 | A | 11/1996 | Hubbell et al. |
| 5,593,839 | A | 1/1997 | Hubbell et al. |
| 6,620,584 | B1 | 9/2003 | Chee et al. |
| 7,569,343 | B2 | 8/2009 | Marton et al. |
| 9,970,932 | B2 | 5/2018 | Woodbury et al. |
| 10,006,919 | B2 | 6/2018 | Woodbury et al. |
| 2004/0265923 | A1 | 12/2004 | Gilmore et al. |
| 2005/0037398 | A1 | 2/2005 | Gelfand et al. |
| 2005/0186580 | A1 | 8/2005 | Dellinger et al. |
| 2006/0160234 | A1 | 7/2006 | Lopez-Avila et al. |
| 2006/0166199 | A1 | 7/2006 | Marton et al. |
| 2006/0282221 | A1 | 12/2006 | Shah et al. |
| 2008/0157786 | A1 | 7/2008 | Holt et al. |
| 2012/0029056 | A1 | 2/2012 | Alevizos et al. |
| 2014/0080721 | A1 | 3/2014 | Klausing et al. |
| 2018/0259510 | A1 | 9/2018 | Woodbury et al. |

FOREIGN PATENT DOCUMENTS

| | | |
|---|---|---|
| EP | 0476014 A1 | 3/1992 |
| EP | 0624059 A1 | 11/1994 |
| EP | 0728520 A1 | 8/1996 |
| KR | 1020110046865 | 5/2011 |
| WO | WO-9306121 A1 | 4/1993 |
| WO | WO-9408051 A1 | 4/1994 |
| WO | WO-9512608 A1 | 5/1995 |
| WO | WO-9530642 A1 | 11/1995 |
| WO | WO-9535503 A1 | 12/1995 |
| WO | WO-03029459 A2 | 4/2003 |
| WO | WO-2004003233 A1 | 1/2004 |
| WO | WO-2007018656 A2 | 2/2007 |
| WO | WO-2008048970 A2 | 4/2008 |
| WO | WO-2009140039 A2 | 11/2009 |

OTHER PUBLICATIONS

Shin et al ( J. Comb. Chem. 12:463-471) (Year: 2010).*
Breitling F. et al. High-density peptide arrays. Mol. BioSyst., vol. 5, pp. 224-234, 2009.
Cretich, M. et al. Protein and peptide arrays: recent trends and new directions. Biomol Eng. vol. 23, No. 2-3, pp. 77-88, Jun. 2006.
Fodor. Multiplexed biochemical assays with biological chips. Nature 364:555-556 (1993).
Furlong, S.T. et al. Synthesis and physical characterization of a P1 arginine combinatorial library, and its application to the determination of the substrate specificity of serine peptidases. Bioorganic & Medicinal Chemistry, 10(11):3637-3647 (Nov. 2002).
Greving et al., Feature-level MALDI-MS characterization of in situ-synthesized peptide microarrays, Langmuir, Feb. 2009, 1456-1459, vol. 26, No. 3.
Huang, Hung-Chung, et al. Discovering Disease-specific Biomarker Genes for Cancer Diagnosis and Prognosis. Technology in Cancer Research and Treatment 9(3):219-229 (Jun. 2010).
International Application No. PCT/US2014/028771 International Preliminary Report on Patentability and Written Opinion dated Sep. 24, 2015.
International Application No. PCT/US2014/028771 International Search Report and Written Opinion dated Jul. 17, 2014.
International Application No. PCT/US2014/029822 International Preliminary Report on Patentability and Written Opinion dated Sep. 15, 2015.
International Application No. PCT/US2014/029822 International Search Report and Written Opinion dated Sep. 2, 2014.
Min et al. Peptide arrays: towards routine implementation. Current Opinion in Chemical Biology vol. 8, pp. 554-558, 2004.
Stafford P, and Johnston, Microarray technology displays the complexities of the humoral immune response. Expert Rev. Mol. Diagn. vol. 11, No. 1, pp. 5-8, Jan. 2011.
U.S. Appl. No. 14/773,750 Advisory Office Action dated Aug. 10, 2017.
U.S. Appl. No. 14/773,750 Corrected Notice of Allowance dated Mar. 16, 2018.
U.S. Appl. No. 14/773,750 Final Office Action dated Apr. 27, 2017.
U.S. Appl. No. 14/773,750 Non-Final Office Action dated Sep. 26, 2017.

(Continued)

*Primary Examiner* — Christopher M Gross
(74) *Attorney, Agent, or Firm* — Wilson Sonsini Goodrich & Rosati

(57) ABSTRACT

The present application provides arrays for use in immunosignaturing and quality control of such arrays. Also disclosed are peptide arrays and uses thereof for diagnostics, therapeutics and research.

20 Claims, 7 Drawing Sheets

(56) References Cited

OTHER PUBLICATIONS

U.S. Appl. No. 14/773,750 Office Action dated Aug. 10, 2016.
U.S. Appl. No. 14/773,751 Advisory Office Action dated Jan. 9, 2017.
"U.S. Appl. No. 14/773,751 Advisory Office Action dated Sep. 1, 2017".
U.S. Appl. No. 14/773,751 Final Office Action dated Jun. 14, 2017.
U.S. Appl. No. 14/773,751 Final Office Action dated Sep. 29, 2017.
U.S. Appl. No. 14/773,751 Office Action dated Feb. 24, 2017.
U.S. Appl. No. 14/773,751 Final Office Action dated Sep. 19, 2016.
U.S. Appl. No. 14/773,751 Non-Final Office Action dated May 20, 2016.
U.S. Appl. No. 14/773,751 Notice of Allowance dated Jan. 11, 2018.

* cited by examiner

PEPTIDE ARRAY QUALITY CONTROL

CROSS-REFERENCE

This application is a continuation of U.S. application Ser. No. 14/773,750, filed on Sep. 8, 2015, which is a U.S. National Phase Application of PCT/US2014/029822, filed on Mar. 14, 2014, which claims priority to U.S. Provisional Application No. 61/799,494, filed on Mar. 15, 2013, which is incorporated by reference herein its entirety.

STATEMENT AS TO FEDERALLY SPONSORED RESEARCH

This invention was made with government support under Grant No. HDTRA1-11-1-0010 and Contract No. HDTRA1-12-C-0058 awarded by the Defense Threat Reduction Agency. The government has certain rights in the invention.

BACKGROUND OF THE INVENTION

Screening mechanisms may be used for assessing samples for changes in polynucleotide and/or polypeptide concentration and/or expression. While there are some peptide arrays available commercially, such arrays have low density and relatively low fidelity.

SUMMARY OF THE INVENTION

Disclosed herein are methods, components and compositions for determining the quality of a biopolymer array of interest in the context of performing diagnostic assays. The methods, components and compositions disclosed herein can be used to assess or determine if a biopolymer array has sufficient fidelity, density and/or other characteristics necessary for performing diagnostic assays on the biopolymer arrays. The disclosed embodiments can be used as a primary quality control method, or can be used in conjunction with other quality control methods for assessing the quality of a biopolymer array of interest.

Accordingly, disclosed herein are methods for determining the quality of a biopolymer array of interest. The biopolymer array may comprise a plurality of molecules coupled to the surface of the array, wherein the molecules are synthesized in situ. In some embodiments, the methods can be used to determine the quality of a biopolymer array prior to initiating a diagnostic procedure on the array. In other embodiments, the methods can be used to determine the quality of a biopolymer array concurrently with a diagnostic procedure, for example, for assessing the immunosignature of a subject or patient. In some embodiments, the subject is a mammal, avian or reptile. In other embodiments, the subject is human. In still other embodiments, the subject is a livestock animal, e.g., bovine, porcine or ovine species, dog, cat, bird, or other domestic or wild animal.

In one aspect, the methods, components and compositions disclosed herein provide for the assessment of the quality of a biopolymer array of interest by providing an array of compounds, incubating the biopolymer array with a biological sample, detecting target binding of the biological components on the array, determining the average target binding values of the biological components to the compounds on the array, and assessing the quality of the array from the average target binding values obtained.

In another aspect, disclosed herein are methods for determining the quality of a biopolymer array of interest, the methods comprising:

a. providing an array of compounds, wherein the compounds are synthesized in situ in a stepwise manner on the surface of the biopolymer array;
b. incubating a biological sample on the biopolymer array;
c. detecting target binding on individual compounds on the biopolymer array;
d. determining the average target binding values of individual compounds affected at each synthesis step; and
f. comparing the average target binding values obtained at each synthesis step to a universal average intensity value for the biopolymer array;
wherein a difference of less than a threshold level between the average target binding values at each synthesis step and the universal average intensity value indicates a failure of the synthesis step in synthesizing the molecules on the array.

In one embodiment, the threshold level is a percent difference between the average target binding values at each synthesis step and the universal average intensity value obtained. In another embodiment, the threshold level indicating failure of the synthesis step is less than about 2%, less than about 5%, less than about 10%, less than about 20%, less than about 25% or less than about 30%. In another embodiment, the threshold level indicating failure of the synthesis step is less than about 20%. In still another embodiment, the threshold level indicating failure of the synthesis step is less than about 10%. In yet another embodiment, the threshold level indicating failure of the synthesis step is less than about 5%.

In some embodiments, the threshold level is a difference in standard error between the average target binding values at each synthesis step and the universal average intensity value obtained. In one embodiment, the threshold level indicating failure of the synthesis step is less than 4× the standard error (SE), less than 3.5×SE, less than 3×SE, less than 2.5×SE or less than 2×SE. In another embodiment, the threshold level indicating failure of the synthesis step is less than 3×SE. In still other embodiments, the threshold level indicating failure of the synthesis step is less than 2.5×SE. In yet other embodiments, the threshold level indicating failure of the synthesis step is less than 2×SE.

In some embodiments, the biopolymer array is a peptide array or a polynucleotide array. In other embodiments, the biopolymer array is a peptide array. In still other embodiments, the peptide array is a random peptide array.

In some embodiments, the compound is a nucleic acid, a peptide, a polymer, a lipid, a polysaccharide or an analog thereof. In still other embodiments, the compound is a peptide. In yet other embodiments, the peptides are synthesized in situ on the array surface. In some embodiments, the peptide length is between 10-25 amino acid residues. In still other embodiments, the peptide length is between 15-20 amino acid residues. In yet other embodiments, the peptide spacing within a feature on the array is less than 6 nm, less than 4 nm or less than 2 nm. In yet other embodiments, the biological sample is a blood sample, a serum sample, a plasma sample, a urine sample, a sputum sample, a mucosal sample, a peritoneal fluid sample, a tissue sample, an exudates, an effusion or a biopsy.

Also disclosed herein are methods for determining the quality of a biopolymer array of interest, the methods comprising:

a. providing an array of compounds, wherein the compounds are synthesized in situ in a stepwise manner on the surface of the biopolymer array;

b. incubating a biological sample on the biopolymer array;
c. detecting target binding on individual compounds on the biopolymer array;
d. determining the average target binding values of individual compounds affected at each synthesis step; and
e. comparing the average target binding values obtained at each synthesis step to a universal average intensity value for the biopolymer array;
wherein a difference of greater than a threshold level between the average target binding values at each synthesis step and the universal average intensity value indicates fidelity of the synthesis step and acceptable synthesis of the compounds on the array.

In some embodiments, the threshold level is a percent difference between the average target binding values at each synthesis step and the universal average intensity value obtained. In some embodiments, the threshold level indicating fidelity of the synthesis step is at least over 2%, at least over 3%, at least over 4%, at least over 5%, at least over 6%, at least over 7%, at least over 8%, at least over 9%, at least over 10%, at least over 15%, at least over 20%, at least over 25%, or at least over 30%. In yet other embodiments, the threshold level indicating fidelity of the synthesis step is at least over 25%. In still other embodiments, the threshold level indicating fidelity of the synthesis step is at least over 10%. In one embodiment, the threshold level indicating fidelity of the synthesis step is at least over 5%.

In some embodiments, the threshold level is a difference in standard error between the average target binding values at each synthesis step and the universal average intensity value obtained. In one embodiment, the threshold level indicating fidelity of the synthesis step is at least over 4× the standard error (SE), at least over 3.5×SE, at least over 3×SE, at least over 2.5×SE or at least over 2×SE. In another embodiment, the threshold level indicating fidelity of the synthesis step is at least over 3×SE. In other embodiments, the threshold level indicating fidelity of the synthesis step is at least over 2.5×SE. In yet other embodiments, the threshold level indicating fidelity of the synthesis step is at least over 2×SE.

A method for determining the quality of a biopolymer array of interest, comprising:
a. providing an array of compounds, wherein the compounds are synthesized in situ in a stepwise manner by sequential addition of different components at a specific position in b. the compound on the surface of the biopolymer array;
c. incubating a biological sample on the biopolymer array;
d. detecting target binding on individual compounds on the biopolymer array;
e. determining the average target binding values of each component at a specific position in individual compounds synthesized on the array; and
f. comparing the average target binding values obtained for each component at each position in individual compounds synthesized to a universal average intensity value for the biopolymer array;
wherein a difference of less than a threshold level between the average target binding values for each component at each position in individual compounds synthesized and the universal average intensity value indicates a failure of a synthesis step for the compounds on the array.

In one embodiment, the threshold level is a percent difference between the average target binding values at each position in individual compounds synthesized and the universal average intensity value obtained. In some embodiments, the threshold level indicating failure of the synthesis step is less than about 2%, less than about 5%, less than about 10%, less than about 20%, less than about 25% or less than about 30%. In yet other embodiments, the threshold level indicating failure of the synthesis step is less than about 20%. In still other embodiments, the threshold level indicating failure of the synthesis step is less than about 10%. In yet other embodiments, the threshold level indicating failure of the synthesis step is less than about 5%.

In some embodiments, the threshold level is a difference in standard error between the average target binding values at each position in individual compounds synthesized and the universal average intensity value obtained. In other embodiments, the threshold level indicating failure of the synthesis step is less than 4× the standard error (SE), less than 3.5×SE, less than 3×SE, less than 2.5×SE or less than 2×SE. In still other embodiments, the threshold level indicating failure of the synthesis step is less than 3×SE. In still other embodiments, the threshold level indicating failure of the synthesis step is less than 2.5×SE. In still other embodiments, the threshold level indicating failure of the synthesis step is less than 2×SE.

In some embodiments, the biopolymer array is a peptide array or a polynucleotide array. In yet other embodiments, the biopolymer array is a peptide array. In some embodiments, the peptide array is a random peptide array. In yet other embodiments, the compound is a nucleic acid, a peptide, a polymer, a lipid, a polysaccharide or an analog thereof. In still other embodiments, the compound is a peptide.

In yet other embodiments, the peptides are synthesized in situ on the array surface. In still other embodiments, the peptide length is between 10-25 amino acid residues. In yet other embodiments, the peptide length is between 15-20 amino acid residues. In one embodiment, the peptide spacing within a feature on the array is less than 6 nm, less than 4 nm or less than 2 nm. In another embodiment, the biological sample is a blood sample, a serum sample, a plasma sample, a urine sample, a sputum sample, a mucosal sample, a peritoneal fluid sample, a tissue sample, an exudates, an effusion or a biopsy.

Also disclosed herein are methods for determining the quality of a biopolymer array of interest, comprising:
a. providing an array of compounds, wherein the compounds are synthesized in situ in a b. stepwise manner by sequential addition of different components at a specific position in the compound on the surface of the biopolymer array;
c. incubating a biological sample on the biopolymer array;
d. detecting target binding on individual compounds on the biopolymer array;
e. determining the average target binding values of each component at a specific position in individual compounds synthesized on the array; and
f. comparing the average target binding values obtained for each component at each position in individual compounds synthesized to a universal average intensity value for the biopolymer array;
wherein a difference of greater than a threshold level between the average target binding values for each component at each position in individual compounds synthesized and the universal average intensity value indicates a fidelity of a synthesis step for the compounds on the array.

In one embodiment, the threshold level is a percent difference between the average target binding values at each position in individual compounds synthesized and the universal average intensity value obtained. In another embodiment, the threshold level indicating fidelity of the synthesis step is at least over 2%, at least over 3%, at least over 4%, at least over 5%, at least over 6%, at least over 7%, at least over 8%, at least over 9%, at least over 10%, at least over 15%, at least over 20%, at least over 25%, or at least over 30%. In yet another embodiment, the threshold level indicating fidelity of the synthesis step is at least over 25%. In still another embodiment, the threshold level indicating fidelity of the synthesis step is at least over 10%. In yet another embodiment, the threshold level indicating fidelity of the synthesis step is at least over 5%.

In one embodiment, the threshold level is a difference in standard error between the average target binding values at each synthesis step and the universal average intensity value obtained. In one embodiment, the threshold level indicating fidelity of the synthesis step is at least over 4× the standard error (SE), at least over 3.5×SE, at least over 3×SE, at least over 2.5×SE or at least over 2×SE. In another embodiment, the threshold level indicating fidelity of the synthesis step is at least over 3×SE. In still another embodiment, the threshold level indicating fidelity of the synthesis step is at least over 2.5×SE. In yet another embodiment, the threshold level indicating fidelity of the synthesis step is at least over 2×SE.

Also disclosed herein are methods for determining the quality of a biopolymer array of interest, comprising:
a. obtaining a first binding pattern of the array of interest;
b. obtaining a second binding pattern of a reference array;
c. comparing the first binding pattern with the second binding pattern and calculating a correlation value; and
d. determining the quality of the array,
wherein a correlation value of less than a threshold level indicates a fidelity of the biopolymer array.

In one embodiment, the correlation value is a correlation coefficient. In another embodiment, the correlation coefficient is obtained by Pearson Correlation or Spearman rank correlation, or Kolmogorov-Smirnov test. In another embodiment, the threshold level is defined as a percentage of the correlation coefficient between assays.

In one embodiment, the threshold level is at least under 3%, at least under 4%, at least under 5%, at least under 6%, at least under 7%, at least under 8%, at least under 9%, at least under 10%, at least under 15%, at least under 20%, at least under 25%, at least under 30%, at least under 35%, at least under 40%, at least under 45%, or at least under 50%. In yet another embodiment, the threshold level is at least under 3%. In still another embodiment, the threshold level is at least under 5%. In still another embodiment, the threshold level is at least under 10%. In yet another embodiment, the threshold level is at least under 15%.

In one embodiment, the threshold level is defined as a standard deviation derived from calculation of a plurality of correlation coefficients between an assay and a standard assay. In another embodiment, the threshold level is at least under 2×SD, at least under 2.5×SD, at least under 3×SD, at least under 3.5×SD or at least under 4×SD. In still another embodiment, the threshold level is at least under 2×SD. In yet another embodiment, the threshold level is at least under 3×SD. In still another embodiment, the threshold level is at least under 4×SD.

In one embodiment, the first binding pattern is obtained from a subset of biopolymers on the array of interest, and the second binding pattern is obtained from a corresponding subset of biopolymers on the reference array. In another embodiment, the first binding pattern is obtained from binding with a first sample, the second binding pattern is obtained from binding with a second sample, wherein the first sample and the second sample are from the same species. In yet another embodiment, the first sample and second sample are not from the same subject. In still another embodiment, the species is human being. In yet another embodiment, the first sample and second sample are a blood sample.

Also included herein are methods for determining the quality of a batch of biopolymer arrays, comprising:
a. obtaining a binding pattern of at least two arrays of a batch;
b. obtaining a correlation value of the binding pattern between the at least two arrays; and
c. comparing the correlation value with a correlation range.
wherein a correlation value of less than a threshold level indicates a fidelity of the biopolymer array.

In one embodiment, the correlation values of the binding patterns are obtained between all possible pairs of arrays of the batch. In another embodiment, the correlation value is a correlation coefficient. In still another embodiment, the correlation coefficient is obtained by Pearson Correlation or Spearman rank correlation, or Kolmogorov-Smirnov test.

In one embodiment, the threshold level is defined as a percentage of the correlation coefficient between assays. In yet another embodiment, the threshold level is at least under 3%, at least under 4%, at least under 5%, at least under 6%, at least under 7%, at least under 8%, at least under 9%, at least under 10%, at least under 15%, at least under 20%, at least under 25%, at least under 30%, at least under 35%, at least under 40%, at least under 45%, or at least under 50%. In still another embodiment, the threshold level is at least under 3%. In still another embodiment, the threshold level is at least under 5%. In yet another embodiment, the threshold level is at least under 10%. In yet another embodiment, the threshold level is at least under 15%.

In one embodiment, the threshold level is defined as a standard deviation derived from calculation of a plurality of correlation coefficients between an assay and a standard assay. In yet another embodiment, the threshold level is at least under 2×SD, at least under 2.5×SD, at least under 3×SD, at least under 3.5×SD or at least under 4×SD. In yet another embodiment, the threshold level is at least under 2×SD. In yet another embodiment, the threshold level is at least under 3×SD. In still another embodiment, the threshold level is at least under 4×SD.

INCORPORATION BY REFERENCE

All publications, patents, and patent applications mentioned in this specification are herein incorporated by reference to the same extent as if each individual publication, patent, or patent application was specifically and individually indicated to be incorporated by reference. If more than one version of a sequence is associated with a deposit number at different times, the version associated with the deposit number at the effective time of filing the application is meant.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
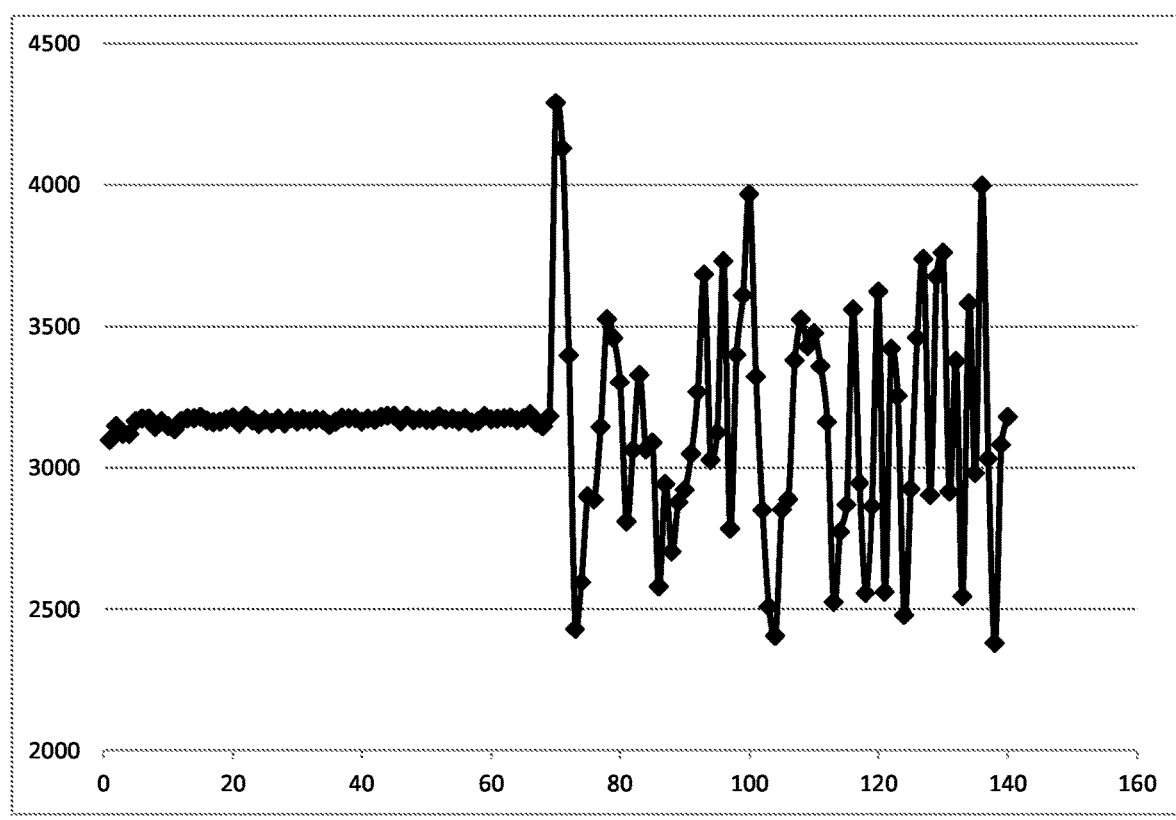
FIG. 1 illustrates average intensity vs. step number (mask number).

Specific binding refers to the binding of a compound to a target (e.g., a component of a sample) that is detectably higher in magnitude and distinguishable from non-specific binding occurring to at least one unrelated target. Specific binding can be the result of multiple, structurally specific interactions between particular chemical groups in the ligand and its binding partner or a particular spatial fit (e.g., lock and key type) whereas nonspecific binding is usually the result of interactions in which there is not particular spatial arrangement of the ligand relative to its binding partner (e.g., general hydrophobic or charge-charge interactions that do not result in a specific structure of the binding pair). Specific binding does not however imply that a compound binds one and only one target. Thus, a compound can and often does show specific binding of different strengths to several different targets and only nonspecific binding to other targets. Preferably, different degrees of specific binding can be distinguished from one another as can specific binding from nonspecific binding. Specific binding often involves an apparent association constant of $10^3$ or higher, where the concentrations of components in the unit-less association constant are defined relative to their standard states (this is true for all association constant values listed in this specification).

An association constant is an equilibrium constant for the binding reaction between a ligand (L) and its binding partner (B): L+B$\leftarrow$$\rightarrow$LB, $$K_{assoc} = \frac{\left(\frac{LB}{LB_0}\right)}{\left(\frac{L}{L_0} \times \frac{B}{B_0}\right)}$$

where L, B and LB in this equation are the concentrations of the ligand, binding partner and the ligand/binding partner complex, respectively, and $L_0$, $B_0$ and $LB_0$ are the standard state concentrations of ligand, binding partner and the ligand/binding partner complex, respectively. The dissociation constant for the same binding interaction would be given by $1/K_{assoc}$. The term "apparent association constant" refers to the value calculated for $K_{assoc}$ as defined above under conditions where one or more binding partner molecules are confined spatially, such as on a surface, such that multiple binding partners are in close enough proximity to act in concert or the confined environment, such as a surface alters the nature of the interaction between the ligand and the binding partner. The term "apparent dissociation constant" refers to the inverse of the apparent association constant. In the text contained in this document, the use of the terms "association constant" or "dissociation constant" may include both true and apparent association and dissociation constants.

Specific binding can additionally or alternatively be defined as a binding strength (e.g., fluorescence intensity) more than three standard deviations greater than background represented by the mean binding strength of empty control areas in an array (i.e., having no compound, where any binding is nonspecific binding to the support). The range of affinities or avidities of compounds showing specific binding to a monoclonal or other sample can vary by from about 1 to about 4 and often from about 2.5 to about 3.5 orders of magnitude. An apparent association constant includes avidity effects if present (in other words, if a target shows enhanced affinity to multiple molecules of the same compound, the apparent association constant is a value reflecting the aggregate binding of the multiple molecules of the same compound to the target). When contacted with a random selection of monoclonal antibodies, a subset of compounds (e.g., from about 1 to about 20, or from about 5 to about 15%) have association constants in the range of from about $10^3$ to about $10^6$, from about $2\times10^3$ to about $10^6$ or from about $10^4$ to about $10^6$ to at least one and sometimes several (e.g., at least about 2, about 5 or about 10) different targets. A subset of all peptides or other compounds (e.g., at least about 1%, at least about 5% or about 10%; from about 1 to about 75%, from about 5 to about 60%, from about 1 to about 20% or from about 5 to about 15%) usually shows actual association constants of from about $10^3$ to about $10^6$ to at least one and usually several targets (e.g., at least about 2, about 5 or about 10). The same ranges of association constant apply to composite targets binding to the same compound in a complex sample. Of course different compounds in an array have different degrees of binding strength to components of a sample and some compounds can bind with higher or lower apparent association constants than these ranges.

Avidity is defined as enhanced binding of a component in solution to a surface that includes multiple copies of a compound, such as a peptide, that the solution component has affinity for. In other words, given a compound on a surface that individually has some affinity for a component of a solution, avidity reflects the enhanced apparent affinity that arises when multiple copies of the compound are present on the surface in close proximity. Avidity is distinct from cooperative binding in that the interaction does not involve simultaneous binding of a particular molecule from the solution to multiple molecules of the compound on the surface. Avidity interactions and/or cooperative binding can occur during the association of components of a solution, such as antibodies in blood, with compounds on a surface.

Patients include humans, veterinary animals, such as cats, dogs, horses, farm animals, such as chickens, pigs, sheep, cattle and laboratory animals, such as rodents, e.g., mice and rats.

A binding profile of an array is a measure of the amount of component(s) of a sample bound to the different compounds of an array to a particular sample. The amount of component(s) bound reflects the amount of the components in the sample as well as the binding strength of components to the compounds. A binding profile can be represented for example as a matrix of binding strengths corresponding to the different compounds in an array. A binding profile typically includes binding strengths of a plurality of compounds (e.g., at least 2, 10, 50, 100 or 1000 having dissociation constants in a range of from about $10^{-3}$ to about $10^{-6}$ to a sample).

Binding strength can be measured by association constant, dissociation constant, dissociation rate, or association rate, or a composite measure of affinity which may include one or more of these measures. The strength of a signal from a labeled component of a sample bound to immobilized compounds can provide a value for general affinity. If a term used to define binding strength is referred to as "apparent" what is meant is a measured value without regard to multivalent binding. For example, the measured value of an association constant under conditions of multivalent binding includes a plurality of effects due to monovalent binding, among other factors. Unless otherwise specified, binding strength can refer to any of these measures referred to above.

The term "nucleic acids" includes any and all forms of alternative nucleic acid containing modified bases, sugars, and backbones including peptide nucleic acids and aptamers, optionally, with stem loop structures.

The term "polypeptide" is used interchangeably with "peptide" and in its broadest sense to refer to a sequence of subunit natural amino acids, amino acid analogs including unnatural amino acids. Peptides include polymers of amino acids having the formula $H_2NCHRCOOH$ ($\alpha$-amino acids), the formula $H_2NCHRCHRCOOH$ ($\beta$-amino acids) and/or analog amino acids having the formula $HRNCH_2COOH$. The subunits are linked by peptide bonds (i.e., amide bonds), except as noted. Often all subunits are connected by peptide bonds. The polypeptides may be naturally occurring, processed forms of naturally occurring polypeptides (such as by enzymatic digestion), chemically synthesized or recombinantly expressed. Preferably, the polypeptides are chemically synthesized using standard techniques. The polypeptides may comprise D-amino acids (which are resistant to L-amino acid-specific proteases), a combination of D- and L-amino acids, beta amino acids, and various other "designer" amino acids (e.g., beta-methyl amino acids, Ca-methyl amino acids, and N$\alpha$-methyl amino acids) to convey special properties. Synthetic amino acids include ornithine for lysine, and norleucine for leucine or isoleucine. Hundreds of different amino acid analogs are commercially available from e.g., PepTech Corp., MA. In general, unnatural amino acids have the same basic chemical structure as a naturally occurring amino acid, i.e., an a carbon that is bound to a hydrogen, a carboxyl group, an amino group, and an R group.

In addition, polypeptides can have non-peptide bonds, such as N-methylated bonds (—N(CH$_3$)—CO—), ester bonds (—C(R)H—C—O—O—C(R)—N—), ketomethylen bonds (—CO—CH$_2$—), aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain. These modifications can occur at any of the bonds along the peptide chain and even at several (2-3) at the same time. For example, a peptide can include an ester bond. A polypeptide can also incorporate a reduced peptide bond, i.e., $R_1$—CH$_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. The compounds can also be peptoids (N-substituted glycines), in which the sidechains are appended to nitrogen atoms along the molecule's backbone, rather than to the $\alpha$-carbons, as in amino acids.

The term "polysaccharide" means any polymer (homopolymer or heteropolymer) made of subunit monosaccharides, oligimers or modified monosaccharides. The linkages between sugars can include acetal linkages (glycosidic bonds), ester linkages (including phophodiester linkages), amide linkages, and ether linkages.

General

The invention provides arrays of compounds, and methods of analyzing the arrays, for use in profiling samples. The arrays include compounds binding to components of the samples at relatively low affinities. Although practice of the invention is not dependent on an understanding of mechanism, it is believed that under conditions of monovalent binding, different degrees of specific binding might be difficult to distinguish from each other and from nonspecific binding. However, the affinity of compounds binding to components of the samples can be increased by forming arrays such that components of the samples (e.g., antibodies or cells) can bind to more than one molecule of a compound at the same time or through avidity interactions with high densities of the compounds on the surface. When a sample is applied to an array under such conditions, the compounds of the array bind to component(s) of the sample with significantly different affinities generating a profile characteristic of the sample. Such a profile usually includes some compounds having no specific binding to components of the sample and other compounds having different degrees of specific binding to components of the sample. Although such binding interactions are specific in the sense that overall binding profiles of an array are reproducible for replicates of the same sample and distinguishable between different samples, they are not necessarily unique in that compounds in the array usually show specific binding albeit of different degrees to a number of different components of a sample or different samples.

The affinity or apparent affinity of informative compounds (i.e., those showing distinguishable binding to different targets) in an array can be measured for monoclonal antibody samples. When measured against monoclonal antibodies that do not bind to a selected target, informative compounds in some arrays often show apparent affinity association constants in a range of from about $10^4$ to about $10^9$, from about $10^6$ to about $10^9$, from about $10^4$ to about $10^7$, or from about $10^4$ to about $10^6$. Association constants of such informative compounds are often within a range of from about $10^3$ to about $10^6$, or from about $10^4$ to about $10^5$. When measured against a complex sample, similar ranges of apparent or actual association constants are observed; however, in this case, the constants are a composite of values for multiple different components within a sample binding to the same compound. Such affinities can be distinguished from nonspecific interactions. The proportion of informative compounds (i.e., compounds that show distinguishable binding among different targets) can vary depending on the composition of the array and the sample, but ranges of from about 0.1 to about 50%, from about 1 to about 30%, from about 0.1 to about 20%, from about 1 to about 15%, or about 3 to about 12% provide some guide. Given that monoclonal antibodies each have their own signature consisting of binding to many compounds on the surface, it might have seemed impossible to meaningfully resolve patient serum samples which may contain $10^8$ or more distinct antibodies with different binding specificities. When an array is hybridized against a complex sample, such as from a patient or subject, the binding profile represents the aggregate effect of multiple components of a sample. Surprisingly despite the complexity of the samples, different samples are associated with different binding profiles. Also surprisingly, the intensity of binding profile often differs between patients with a disease or at risk of disease relative to normal patients.

The binding profile of such an array to a sample can be used to characterize a sample. For example, the binding profile can be compared with binding profiles known to be associated with different diseases or stages of diseases or lack of diseases. Alternatively or additionally, the binding can be analyzed, for example, by using a compound binding relatively strongly to a component of the sample to affinity purify an antibody from the sample, or by comparing the sequence of a peptide in the array known to bind strongly to a component of a sample with a protein database to identify a protein in the sample. Remarkably, the same array can generate different and informative profiles with many different samples representing different disease states, disease stages, lack of disease and the like. Moreover, a profile characteristic of disease or departure from a non-disease state can be detected very early in development of a disease before typical analytical markers of disease would be detectable by conventional methods, such as ELISA.

Immunosignaturing

The present application provides methods for improved quality control (QC) of arrays in the form of imumunosignaturing.

In the process of immunosignaturing (see, e.g., Stafford and Johnson "Microarray technology displays the complexities of the humoral immune response," *Exp. Rev. Mol. Diagn.* 11:5-8 (2011)), a sample of blood is applied to a large number of peptides or other molecular heteropolymers each associated with a feature on a surface (for example, an array of features each having a different peptide or group of peptides associated with it). The antibodies in the blood bind differentially to the molecular species in each of the features. This forms a pattern of binding that provides a detailed insight into the molecular recognition profile of the antibodies in the blood. The concept is that any change in health is likely to be represented by a change in this molecular recognition profile.

The patterned molecular surfaces that measure the molecular recognition profile can be created in a number of different ways. It is useful to have methods of determining the quality of these surfaces after manufacturing. The present inventors developed methods that are particularly useful if the immunosignaturing data from the array itself serves as the measure of the surface quality of the array.

Overall Correlation Coefficient

The vast majority of the antibody signals on the immunosignature arrays do not change substantially between healthy individuals and individuals with a particular disease. Thus, in most cases, the correlation coefficient (or any other measure of overall correlation) between different peptide arrays is generally high and does not change greatly with the identity of the blood sample. The present inventors identified for the first time that one approach to assessing the quality of an array is to compare correlation coefficient values (or some other numerical evaluation of correlation between samples) and set a particular range for an acceptable correlation.

Another variation of this approach is to ask directly how many of the peptides or molecular species show similar or different binding between the array in question and a reference array. This can be done by a direct comparison, peptide by peptide, looking for the number of peptides that are substantially different between arrays. This can be done, for example, by having generated data from enough reference arrays to have determined the standard deviation for each peptide. One can then ask where each peptide in the array in question ranks relative to the average and standard deviation. The number of peptides within 1 or 2 standard deviations can be used as an indication of how well correlated the intensities in the arrays are.

Relating Array Binding Intensity Pattern to Fabrication Sequence

Generally speaking, the arrays used for immunosignaturing are made using different heteropolymers or sets of molecules creating by linking a common set of monomers together in a specific order or chemical linkage pattern.

One can represent any such library of molecules in terms of a type of monomer at each position in the heteropolymer. For example, one can talk about a peptide in terms of the position in the amino acid sequence and the identity of the amino acid placed there.

For relatively large libraries, it becomes possible to ask the question: did a particular monomer in a particular position have the expected effect on average binding to the array? Thus, one can average the intensity for every heteropolymer in which position i is occupied by monomer j and get a value. If the number of peptides is large enough, that value will be statistically different from the average value of the intensity for all heteropolymers on the array and contains information about the effect of a particular type of monomer at a particular position. In the case of in situ fabricated arrays, this often corresponds to a fabrication step.

For example, the peptides with an alanine at position 7 in the peptide may all derive from the same fabrication step. If that step failed, then it will either have no effect (the peptides containing that amino acid at that position in their theoretical sequence will no longer have a statistically detectable effect) or the nature and magnitude of the effect may change from the empirically determined effect. In general, the intensities of the peptides or heteropolymers to which a particular monomer is added by a particular cycle of a synthetic process can be averaged, and compared to the average value of all peptides or heteropolymers in order to determine whether that particular monomer is statistically different from all peptides or heteropolymers, and if so, what the new direction and magnitude is.

Non-limiting examples of statistical methods that can be performed to determine a binding intensity of a sample to an array of the invention include: a) analysis of variance (ANOVA); b) chi-squared test; c) factor analysis; d) Mann-Whitney U analysis; e) mean square weighted deviation (MSWD); f) Pearson product-moment correlation coefficient; g) regression analysis; h) spearman's rank correlation coefficient; i) student's t-test; j) time series analysis; k) Kolmogorov-Smirnov test; l) likelihood analysis; and m) Mixture models.

Compounds for Use in Arrays

Many different classes of compounds or combinations of classes of compounds can be used for the arrays and methods of the invention. Classes of compounds include nucleic acids and their analogs, polypeptides (broadly defined as above), polysaccharides, organic compounds, inorganic compounds, polymers, lipids, and combinations thereof. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). The test compounds can be natural or synthetic. The compounds can be naturally occurring or non-naturally occurring. Many different classes of compounds other than nucleic acids can be used, but optionally if the compounds are nucleic acids, the sample components detected are not nucleic acids. In some arrays, the test compounds have a molecular weight of between about 500 and about 10,000 Da, and optionally between about 1000 to about 4000 Da.

The number of compounds used is a balance between two factors. The more compounds, the more likely an array will include members having detectable affinity for any target of interest. However, a larger number of compounds also increases the cost of synthesizing and analyzing an array. Arrays typically have at least 100 compounds. Arrays having between 500 and 500,000 compounds provide a compromise between likelihood of obtaining compounds with detectable binding to any target of interest and ease of synthesis and analysis. Arrays having, for example, 100 to 500,000 members or 500-500,000, or 1000-250,000 members can also be used. Arrays having, for example, between 10,000 and 100,000, between 25,000 and 500,000 or between 50,000 and 350,000 are also contemplated within the disclosures herein. Alternatively, arrays having much larger numbers of members for example, $10^2$-$10^7$ or 1000 to 5,000,000 or 500,000 to 2,000,000 can also be used. Such arrays typically represent only a very small proportion of total structural space, for example less than $10^{-6}$, $10^{-10}$, or $10^{-15}$ in the case of peptides.

Sequence space means the total number of permutations of sequence of a given set of monomers. For example, for the set of 20 natural amino acids there are $20^n$ permutations, where n is the length of a peptide. Although it is widely assumed that most if not all of the residues in a peptide epitope participate in binding to the a target, it is much more likely that between two and five residues in a 10-12 mer epitope are involved in energetically favorable interactions with the target, the other residues are simply there to adjust the positions of the important residues, and to prevent inhibition of binding. Therefore, a relatively small fraction of the total number of possible peptides can provide a good representation of total sequence space, and include members capable of specific, lower affinity interactions with a wide variety of targets. For example, 500-500,000 random peptides can sample the shape space of an immune system ($10^7$ to $10^8$ antibodies in humans) well enough to distinguish between patients with a disease and patients without.

More compounds in the array should allow higher resolution of the diversity of compounds in the complex sample. For example, an array of 1 million compounds should allow more resolution of complex samples, including reflecting the complexity of antibodies in a subject's sample. Yet, even with a much smaller number of compounds, one is able to detect and identify immune responses from infection or immunization.

For polymeric compounds, the lengths of polymers represent a compromise between binding affinity and ease of synthesis. Length of peptides can affect both the affinity and specificity of binding. However, as peptide length increases the chances that any particular binding event will utilize the entire peptide sequence effectively decreases. Cost of synthesis also increases with increasing length while fidelity of synthesis generally decreases. For peptide arrays, peptides having 4-35, 12-35, 15-25 or 9-20 residues are preferred. These ranges of monomer lengths can also be used for other polymers, although aptamers usually have longer lengths (e.g., up to 100 nucleotides).

The compounds (e.g., all or at least 80, 90 or 95%) are typically chosen without regard to the identity of a particular target or natural ligand(s) to the target. In other words, the composition of an array is typically not chosen because of a priori knowledge that particular compounds bind to a particular target or have significant sequence identity either with the target or known ligands thereto. A sequence identity between a peptide and a natural sequence (e.g., a target or ligand) is considered significant if at least 30% of the residues in the peptide are identical to corresponding residues in the natural sequence when maximally aligned as measured using a BLAST or BLAST 2.0 sequence comparison algorithm with default parameters described below, or by manual alignment and visual inspection (see, e.g., NCBI web site ncbi.nlm.nih.gov/BLAST or the like). Because no particular target is used in the design of the arrays (the arrays are designed to broadly cover the space of molecular recognition), essentially any target will bind to the array and form a signature.

Some compounds are randomly selected from total sequence space or a portion thereof (e.g., peptides in which certain amino acids are absent or under-represented). Random selection can be completely random in which case any compound has an equal chance of being selected from sequence space or partially random in which case the selection involves random choices but is biased toward or against certain monomers, such as amino acids. Random selection of peptides can be made for example by a pseudorandom computer algorithm. The randomization process can be designed such that different amino acids are equally represented in the resulting peptides, or occur in proportions representing those in nature, or in any desired proportions.

In some instances, cysteine residues are omitted from library members with the possible exception of a terminal amino acid, which provides a point of attachment to a support. In some libraries, certain amino acids are held constant in all peptides. For example, in some libraries, the three C-terminal amino acids are glycine, serine and cysteine with cysteine being the final amino acid at the C-terminus. A library chosen by random selection, once selected is of known identity and can be reproduced without repeating the initial random selection process. Nevertheless, the compounds in such library retain the same random relations with one another. For example, the peptides in a random library that is subsequently reproduced retain a random distribution throughout sequence space (with the possible exception of cysteine residues, if this residue is omitted). Collections of compounds, such as peptides, that are randomly distributed over sequence space, are still considered random even if reproduced without repeating the initial random selection.

The principles for selecting peptides and other compounds for arrays in the present methods are analogous to those for selecting initial libraries of compounds in producing synthetic antibodies, as further described in WO/2008/

048970 and WO2009/140039, the disclosures of which are incorporated by reference in its entirety herein.

Making Arrays

Compounds can be pre-synthesized and spotted onto a surface of an array or can be synthesized in situ on an array surface (see, e.g., Cretich et al., *Biomol. Eng.* 2, 77-88 (2006); Min et al., *Current Opinion in Chemical Biology* 8, 554-558 (2004), Breitling, *Mol. BioSyst.*, 5, 224-234 (2009), U.S. Pat. No. 5,143,854; EP 476,014, Fodor et al., 1993, *Nature* 364, 555-556; U.S. Pat. Nos. 5,571,639, 5,593,839, EP 624,059, U.S. Pat. No. 6,620,584, and EP 728,520). Customized arrays are also commercially available from suppliers such as Invitrogen, PEPperPRINT, LC Sciences or Pepscan. The surface is usually derivatized with a functional group that attaches to the compounds, optionally via linker. Compounds can be attached via covalent or noncovalent linkages. The array surface can be a single contiguous surface of a support.

Alternatively an array can be formed by spotting or synthesizing different compounds on different particulate supports, such as beads. Peptides can be attached in either orientation (N or C) relative to the array. In general, the different compounds occupy different areas of a contiguous array or different particles in a particulate array. The identity of which compound occupies which area of an array or which particle is usually either known as a result of the synthesis process or determinable as a result of an encoding process. Encoding processes are commonly used for beads. The different areas in a contiguous array can be immediately adjoining as may arise when such arrays are the result of in situ synthesis, or separated, which is often the result of spotting.

An area or cell of an array is a unit of surface area from which a separate signal is detectable. In some arrays, each area of the array is occupied only by molecules of the same compound except for possibly a small degree of bleed over from one area to another, due for example, to imperfections in the array. In other arrays, some or all of the areas contain a pool of two or more different compounds. In such an array, the signal from an area containing a pool of two or more different compounds is the aggregate undivided signal from the compounds constituting the pool.

Such arrays typically contain from 100-5,000,000 compounds (e.g., 100-1,000,000, 500, 100,000 or 500-25,000 compounds) as discussed above. These numbers of compounds can readily be accommodated in different regions of an array of the order of 0.1-5 cm² combined area.

Within any one area of a contiguous array or within any one particle of a particle array many different molecules of the same compound are present. Because compounds are usually attached to a derivatized surface of a support or particle (e.g., a support or particle bearing a linker), the density of molecules within an area of an array or a particle can be controlled in part by the derivatization process, for example, the period of time and concentration of derivatizing agent used. The density of molecules can also be controlled by the attachment or in situ synthesis process by which a compound is attached to a support. The length of a coupling cycle and concentration of compound used in coupling can both affect compound density.

The density of different molecules of a compound within an area of an array or on a particle controls the average spacing between molecules of a compound (or compounds in the case of a pooled array), which in turn determines whether a compound is able to form enhanced apparent affinity to a sample (an avidity interaction). If two molecules of a compound or compounds in the case of a pooled array, are sufficiently proximate to one another, both molecules can enhance apparent affinity to the same binding partner. For peptides of length 15-25 residues an average (mean) spacing of less than 0.1-6 nm, 1-4 nm, 2-4 nm, e.g., 1, 2 or 3 nm is, for example, suitable to allow different regions of the same compound to undergo binding with enhanced apparent affinity. Average (e.g., mean) spacings are typically less than 6 nm because spacings of 6 nm or more are do not allow avidity to enhance the apparent affinity for the target or cooperative binding to take place. For example, for peptides of lengths 15-25 residues, the two identical binding sites of one antibody could not span more than 6 nm to contact two peptides at once and bind cooperatively. The optimum spacing for enhancing avidity and/or cooperativity interactions may vary depending on the compounds used and the components of the sample being analyzed.

Enhancement of apparent affinity through either cooperative binding or avidity interactions can be shown by several methods, including comparing binding strength of an antibody to an otherwise identical antibody fragment (e.g., a Fab fragment) having only one binding site. Binding strength to the intact antibody that is greater than the antibody fragment (e.g., higher apparent association constant) may differentiate cooperativity from enhanced avidity. Enhancement of binding strength can also be shown by comparing the binding of an array of an immobilized compounds to an intact antibody with two binding sites with the reverse format in which the antibody is immobilized and the compound is in solution. Stronger binding (e.g., higher apparent association constant) of the immobilized compound to the antibody in solution compared with immobilized antibody to the compound in solution provides an indication that the immobilized compound can either form multivalent bonds to the antibody (cooperative binding), or interacts via enhanced avidity. Association constants, or apparent association constants, of compounds can be measured by conventional methods using technologies like SPR, ELISA, Luminex and other solution-phase binding (e.g., monitoring changes in bound signal over time) when the antibody or other sample is immobilized and the compound is in solution. Conversely, apparent association constants can be measured when a compound is immobilized and antibody or other sample is in solution. Once suitable synthesis or deposit conditions have been established for achieving arrays capable of enhanced binding, other arrays can be made under the same conditions without individualized testing.

Usually, different compounds are deposited or synthesized in different areas of an array under the same conditions, so that if one compound is spaced so that it is capable of enhanced avidity binding, most or all compounds are. In some arrays, at least 10%, 50%, 75%, 90% or 100% of compounds in the array are spaced so as to permit enhanced avidity interactions and/or undergo cooperative binding with a binding partner. However, it is not necessary that all compounds be deposited or synthesized with the same spacing of molecules within an area of the array. For example, in some arrays, some compounds are spaced further apart so as not to permit or permit only reduced avidity interactions or cooperative binding compared with other compounds in an array.

The spacing can be measured experimentally under given conditions of deposition by depositing fluorescently labeled compounds and counting photons emitted from an area of an array. The number of photons can be related to the number of molecules of fluorescein in such an area and in turn the number of molecules of compound bearing the label (see, e.g., U.S. Pat. No. 5,143,854). Alternatively, the spacing can be determined by calculation taking into account the number of molecules deposited within an area of an array, coupling efficiency and maximum density of functional groups, if any, to which compounds are being attached. The spacing can also be determined by electron microscopy of an array or via methods sensitive to the composition of molecules on a surface such as x-ray photoelectron spectroscopy or secondary ion mass spectrometry.

Arrays having larger spacing that do not permit cooperative binding or avidity interactions or do so to a reduced extent compared with spacing described above also have application in identifying high affinity interactions. This type of strategy can be used to identify peptides or other compounds, for example, that are very close structurally to the original epitope that raised the antibody response. Alternatively, for arrays of peptides from life space (the set of amino acid sequences represented in the proteins of living organisms), this spacing facilitates identifying the true epitope.

The spacing between compounds can also be controlled using spaced arrays; that is, arrays on surfaces coated with nano-structures that result in more uniform spacing between compounds in an array. For example, NSB Postech amine slides coated with trillions of NanoCone apexes functionalized with primary amino groups spaced at 3-4 nm for a density of 0.05-0.06 per $nm^2$ can be used.

Array formats that can be used include microarrays, beads, columns, dipsticks optical fibers, nitrocellulose, nylon, glass, quartz, mica, diazotized membranes (paper or nylon), silicon, silicones, polyformaldehyde, cellulose, cellulose acetate, paper, ceramics, metals, metalloids, semiconductive materials, quantum dots, coated beads, other chromatographic materials, magnetic particles; plastics and other organic polymers such as polyethylene, polypropylene, and polystyrene; conducting polymers such as polypyrole and polyindole; micro or nanostructured surfaces, nanotube, nanowire, or nanoparticulate decorated surfaces; or porous surfaces or gels such as methacrylates, acrylamides, sugar polymers, cellulose, silicates, and other fibrous or stranded polymers.

An exemplary method of array preparation is as follows. A microarray is prepared by robotically spotting distinct polypeptides on a glass slide having an aminosilane functionalized surface. Each polypeptide has a C-terminal glycine-serine-cysteine as the three C-terminal residues and the remaining (17) residues determined by a pseudorandom computational process in which each of the 20 naturally occurring amino acids except cysteine had an equal probability of being chosen at each position. Polypeptides are conjugated to the aminosilane surface by thiol attachment of the C-terminal cysteine of the polypeptide to a maleimide (sulfo-SMCC, sulfosuccinimidyl 4[N-maleimidomethyl]cyclohexane-1-carboxylate which is covalently bonded to the aminosilane surface. The polypeptides are chemically synthesized, dissolved in dimethyl formamide at a concentration that may range from about 0.1 mg/ml to about 2 mg/ml, and then diluted 4:1 with phosphate-buffered saline prior to spotting. The concentration of peptide or other compound determines the average spacing between peptide molecules within a region of the array. A concentration of 1 mg/ml gives an average spacing of about 0.5 nm. The spacing decreases non-linearly with dilution at lower concentrations. The printed slides stored under an argon atmosphere at 4° C. until use.

An exemplary calculation of spacing is as follows: spot size: 150 µm, spot area: 17671 $µm^2$, nanoprint deposition volume: 200 pL, peptide concentration: 1 mg/ml, deposition amount: 200 pg, # peptides deposited: $8 \times 10^{10}$ per spot, $8 \times 10^{10}$ peptides/17671 $µm^2 = 4.5 \times 10^6$ peptides/$µm^2$, $2.2 \times 10^{-7}$ $µm^2$ area needed by 1 peptide ($4.6 \times 10^{-4}$ µm spacing).

As well as including compounds randomly or without regard to the sample being analyzed, arrays can include other compounds known to bind particular targets, such as proteins, in a sample. These compounds can be antibodies, synbodies or peptides among others. Usually, such interactions are high affinity (e.g., greater than $10^7$, $10^8$ or $10^9$ $M^{-1}$). The number of such known binding partner compounds can be large, for example, there can be a different compound for at least 25, 50, 75, or 90% or substantially all of the known proteins expressed by a given genome, such as the human genome). The different known binding partner compounds occupy different areas of the array in similar fashion to randomly selected compounds. However, because the known binding partner compounds are in general capable of high affinity interactions, they can be used with or without an intermolecular spacing that permits enhanced avidity interactions with the sample. Although one might think that inclusion of compounds selected at random or without regard to the sample being analyzed would be redundant in view of inclusion of known binding proteins to a large part or all of the encoded proteins in a genome, such is not the case because some diagnostic immune responses are the result of somatic mutation or non-protein components and not detected by binding proteins to encoded proteins.

Samples and Components to be Analyzed

The arrays and methods of the invention can be used for analyzing any kind of sample containing or potentially containing analyte(s) of interest. Of particular interest are samples from human or veterinary patients or laboratory model animals. Such samples can be blood (including whole blood, red cells, plasma and the like), urine, feces, saliva, CNS fluid, other body fluids, hair, skin, biopsies and the like. A profile can be obtained from a small volume of sample, e.g., less than, or equal to, for example, 1 µl. Some samples are from patients known or suspected to be suffering from a disease. The identity of the disease may or may not be known. Some samples are obtained from patients known to have been subjected to a risk of disease but in which symptoms of disease are not yet evident. The risk can be genetic (e.g., a particular gene or family history) or experiential (e.g., exposure to a toxic chemical or radiation). Samples can also be obtained from patients who have been vaccinated to analyze the resulting immune response.

Samples from patients can include a wide variety of components subject to potential analysis by an array. The components most amenable to detection are those capable of enhanced avidity interactions to compounds in the array. Such components include antibodies, which can support avidity interactions and/or support cooperative binding through their pairs of heavy and light chains (i.e., two binding sites per antibody) and cells, which can form multiple bonds through multiple copies of receptors displayed from their outer surfaces. Viruses can also form enhanced binding interactions through different copies of coat proteins on their outer surface. Samples from patients can include many different antibodies and/or different cells and/or other components.

Samples can be analyzed with little if any further processing or can be subject to further processing such that only selected components of the sample (e.g., antibodies or cells) are analyzed with the array.

Methods of Detection

Binding interactions between components of a sample and an array can be detected in a variety of formats. In some formats, components of the samples are labeled. The label can be a radioisotype or dye among others. The label can be supplied either by administering the label to a patient before obtaining a sample or by linking the label to the sample or selective component(s) thereof.

Binding interactions can also be detected using a secondary detection reagent, such as an antibody. For example, binding of antibodies in a sample to an array can be detected using a secondary antibody specific for the isotype of an antibody (e.g., IgG (including any of the subtypes, such as IgG1, IgG2, IgG3 and IgG4), IgA, IgM). The secondary antibody is usually labeled and can bind to all antibodies in the sample being analyzed of a particular isotype. Different secondary antibodies can be used having different isotype specificities. Although there is often substantial overlap in compounds bound by antibodies of different isotypes in the same sample, there are also differences in profile.

Binding interactions can also be detected using label-free methods, such as surface plasmon resonance (SPR) and mass spectrometry. SPR can provide a measure of dissociation constants, and dissociation rates. The A-100 Biocore/GE instrument, for example, is suitable for this type of analysis. FLEXchips can be used to analyze up to 400 binding reactions on the same support.

Optionally, binding interactions between component(s) of a sample and the array can be detected in a competition format. A difference in the binding profile of an array to a sample in the presence versus absence of a competitive inhibitor of binding can be useful in characterizing the sample. The competitive inhibitor can be for example, a known protein associated with a disease condition, such as pathogen or antibody to a pathogen. A reduction in binding of member(s) of the array to a sample in the presence of such a competitor provides an indication that the pathogen is present.

The stringency can be adjusted by varying the salts, ionic strength, organic solvent content and temperature at which library members are contacted with the target.

Applications

The arrays have a wide variety of applications in analyzing or characterizing clinical, veterinary, forensic, laboratory and other samples. As with conventional diagnostics, the arrays can be used to identify particular analytes within samples, for example, analytes associated with particular disease. However, the methods can also be used to provide a binding profile of different compounds characterizing a sample. The binding profile represents the aggregate interactions of the compounds with different components in the sample, and can be characteristic of a particular disease, stage of disease or lack of disease. The different components can be complex (e.g., at least 10, 100, 1000 or 1,000,000,000 different antibodies and/or different cells).

A binding profile typically includes compounds whose interactions with the sample are nonspecific as well as compounds whose interaction with the sample reflect specific but low affinity interactions (i.e., apparent or actual dissociation constant between $10^{-3}$ and $10^{-6}$). Compounds with higher affinity interactions (i.e., dissociation constant less than $10^{-6}$) may or may not be present. Such higher affinity interactions if present may arise by chance as a result of a compound in the array being a mimetic of a natural binding partner of a sample component or as a result of including a control in which a compound is a known binding partner of a component of a sample. However, a sample can usually be adequately characterized by the binding profile of compounds with low affinity interactions with the sample, optionally in combination with compounds lacking specific binding to components of the sample. For example, the identity and relative binding of at least 2, 5, 10 or 50 compounds capable of low affinity specific binding to components of the sample can often be used to characterize the sample. Such low affinities actions may in part be the result of compounds serving as mimetopes providing a linear epitope that (imperfectly) resemble an epitope against which an antibody in the same was raised (e.g., a complex 3D-structure).

One application lies in analyzing samples from patients known or suspected to be suffering from a disease but in which the particular disease affecting the patient is not known. A conventional approach would be to perform separate assays for suspected diseases. By contrast, in the present methods, a single binding profile from the patient sample can be used to characterize the patient for many diseases, stage of disease or lack of disease. The binding profile can be used to characterize the sample for virtually any disease, including autoimmune disease, cancer, infectious diseases, and diseases of the CNS. Most if not all diseases involve some change s in antibodies, cells or other components present in patient samples, reflected in a binding profile. Some exemplary infectious diseases include bacterial, fungal and viral diseases, such as Valley Fever, Q-fever, *Tularemia tularensis, Rickettsia rickettsii*, HSV types I and II, HVB, HVC, CMV, Epstein Barr virus, JC virus, influenza, A, B or C, adenovirus, and HIV. Because different infections give different profiles, different infections in a patient having multiple infections can be detected simultaneously. Some exemplary cancers that can be diagnosed or prognosed using the methods of the invention include glioblastoma, breast cancer, multiple independent primary cancer and/or recurrence situation, pancreatic cancer, lung cancer, myeloma, ovarian cancer and esophageal cancer. Precancerous cells that are morphological distinguishable from normal cells but not yet cancerous can also be detected using the methods of the invention. Neurological diseases, such Alzheimer's disease, although not generally considered to be an autoimmune disease, results in some changes in antibodies present in a sample. The same is the case for chronic diseases, such as Asthma, Rheumatoid arthritis, Diabetes mellitus type 1, Psoriasis, Multiple Sclerosis and others.

Another application lies in analyzing samples from patients known or suspected to have a particular disease, but in which the stage, severity or prognosis for the disease is unclear. Again the binding profile can provide an indication of any of these factors.

Another application lies in analyzing samples from vaccinated patients to determine whether an adequate protective immune response is developing. The pattern of response in one patient can be compared, for example, with a patient who has been naturally infected with the pathogen and survived, a similarity of response pattern indicating the patient is likely to survive and a dissimilarity that the patient will get worse or die at least in the absence of alternate treatment. Alternatively, a profile of a patient or animal model immunized with a new vaccine (for example in a clinical or preclinical trial) can be compared with profiles of patients or control animals immunized with an existing vaccine known to be effective. In a further variation, patients being recruited for a clinical trial of a vaccine can be prescreened for binding profile. Those already having a binding profile similar to that of a patient immunized with a vaccine known to be effective or from a patient who has survived a natural infection can be eliminated from the trial because their inclusion might lead to a misleading placebo response.

Another application lies in screening samples from patients who have undergone organ transplant (particularly allotransplantation). The profile in a patient under test can be compared with profiles of patients undergoing organ transplant who have or have not undergone rejection following the transplant. Similarity of the profile between a patient under test and a patient who has previously undergone rejection (or an average profile of a collection of such patients) indicates that the patient is at risk or is undergoing rejection.

Another application lies in analyzing samples from a patient known to be at risk of a disease but in which symptoms of disease are not yet present. The risk can be genetic, such as a genetic mutation associated with disease or family history of the disease, or arise as a result of experience, for example, exposure to a toxic chemical, radiation, traumatic accident, stress, fatigue, chemotherapy, unprotected sex, age, or exposure to a subject with a contagious disease. Such a patient is naturally concerned about the possibility of acquiring a disease and early therapeutic intervention. The methods are particularly useful in crisis situations in which many subjects have had potential exposure to a risk. Conventional diagnostic assays often have a significant lag period before a disease can be developed. For example, conventional viral assays can take several months to develop detectable patient antibodies. Autoimmune diseases (e.g., lupus, type 1 diabetes, rheumatoid arthritis, multiple sclerosis) can take several years to develop specific autoantibody or T-cell responses to specific autoantigens. By contrast, the present methods can detect changes in a profile within a few days (e.g., less than 10, 5 or 3 days) of exposure to a risk, or infection. The changes in binding profile may reflect subtle changes in concentrations of many different components of a sample, few if any of which would be individually detectable. However, in the aggregate, the changes in binding profile of the compounds in the array indicate a change if the risk has started development of disease.

Another application lies in forensic analysis of a sample, for example, a sample recovered from a crime scene or a sample relevant to a paternity analysis. Comparison of a test sample with one or more references samples of known origin can provide an indication of the source of the test sample.

Binding profiles can be used in a variety of ways in characterizing a sample. In some methods, a binding profile of a sample is compared with one or more reference binding profiles of the same compounds. A reference binding profile is a profile that characterizes a particular disease, stage of disease or lack of disease, and the like. Reference profiles are typically determined by averaging binding profiles of several samples (e.g., at least 2, 20, 50 or 100) each characterized for the same disease, stage of disease or lack of disease. Comparison of a sample binding profile with a reference binding profile can involve comparing the different binding strengths of different compounds in an array to the respective samples to derive a value representing the overall similarity of the profiles. A measure of similarity on a scale of similarity is by implication an inverse measure of disimilarity and vice versa. Thus, a value representing the overall similarity includes a value representing the overall disimiliarity. However, mathematically disimiliarity matrices can be handled and analyzed distinctly from similarity matrices. Raw data from the sample being analyzed can of course be normalized before the comparison to eliminate any differences due to sample size, processing, concentration and the like, rather than relative representation of sample components. Standard ANOVA analyses can also block such nuisance factors, provided such factors are accounted for in the experimental design.

Various techniques can be used to derive a value based upon the comparison of a binding profile and a reference binding profile. A derived value can be used to measure the dissimilarity between the binding profile and the reference profile and be evaluated using a distance measure such as the Euclidean Distance (ED) metric. The ED metric is typically used for measuring the distance between two vectors of "n" elements. According to one implementation, if x=(x1, x2, x3, ..., xN) and y=(y1, y2, y3, ..., yN) are two points in Euclidean N-space, then the Euclidean distance between x and j may be computed as:

$$D_{xj} = \text{SquareRoot}(\text{Summation}((x_i - y_i^2)))$$

The ED metric thus not a correlation (0 to 1), but a measurement of dissimilarity.

In the context of comparing a binding profile (defined by its binding values for each point in N-dimensional space, where N is the number of experimental points (conditions)) with a reference binding profile, a ED metric can be determined regardless of the complexity, number of peptides, or number of patients. Each profile being compared may be seen as a pattern: setting an explicit series of points across time, across dilutions, across disease states, across symptoms, etc., and the comparison described here looks for data that reflects this defined series of points.

To standardize the difference between binding profiles being compared, the calculated ED measurement may be normalized by dividing by the square root of the number of conditions as follows:

$$\text{Distance} = |a-b|/\text{square root of } N$$

This is distinct from the aforementioned distance calculation by normalizing for the total number of conditions. This prevents the distance calculation from expanding too far given large numbers of samples.

Accordingly, calculating the Euclidean distance between two data points involves computing the square root of the sum of the squares of the differences between corresponding values. Because the ED metric is a measure of dissimilarity, the distance (d) may be converted, when needed, to a similarity measure as $1/(1+d)$. Distance, similarity, and dissimilarity are interchangeable to a certain degree but each is a uniquely useful given the calculations being applied. As the distance gets larger, the similarity gets smaller. This renders the original data useful for looking at differences in a non-biased and geometrical way. The computation is scalable with increasing number of experiments. In fact, the complexity of the pattern is inherently diminished to the calculation because it is in the denominator and is a square root.

Other distance metrics that can be used include Euclidean Squared, Pearson Correlation, Pearson Squared, Spearman Confidence or Correlation, Kolmogorov-Smirnov test and other like techniques.

Binding profiles can also be used in various analytical methods to further characterize the sample. For example, a compound in the array showing relatively strong binding to the sample (compared with other compounds in the array) can be used to affinity purify a component of the sample. The component can then be further characterized (e.g., by sequencing or immunoreactivity). The identity of the compound may be characteristic of a disease state (e.g., a pathogen, autoantibody or tumor associated antigen). If the component is not already known to be characteristic of a disease state, it can be used as a new target for developing therapies or diagnostics against the disease state. For example, autoantigens or peptides thereof, can be used in inducing tolerance of autoimmune disease. Alternatively, after washing off unbound cellular components, the cellular components binding to an array can be dissociated from the array, fractionated and analyzed in similar fashion. In a further variation, the identity of a compound in the array showing relatively strong binding to a sample can be used to identify a ligand of the component bound in the sample, and hence the component in the sample. For example, if the compounds of the array are peptides, the sequence of a peptide showing relatively strong binding to a sample can be compared with a database of protein sequences. Comparison can be pairwise between a database sequence and a peptide in the array or between a database sequence and a motif or consensus sequence from a plurality of peptides in the array. Sequence similarity to a protein in the database provides an indication that the protein is a ligand of the component in the sample to which the peptide showed strong binding. The identity of a ligand in turn provides at least an indication of potential molecules in the sample and in turn disease states characterized by such molecules.

The same array can be used in any of the applications described above and for virtually any disease or suspected disease state. The same array means either literally the same array, in which case the array may be washed between different samples, or different copies of an array of the same composition. The identity of which compounds in the array are most informative for a disease or other state being analyzed varies by state. Thus, having identified the most informative compounds for a particular disease, derivative arrays or other detection devices and kits can be made that have a reduced number of compounds including the most informative compounds. The derivative arrays are sometimes referred to as secondary arrays to distinguish them from primary arrays used in initial identification of binding compounds and sometimes a sample component bound by these compounds.

A further useful aspect of the present methods is that they can detect not only increased binding of compounds to cellular components in test samples relative to a control sample representing an undiseased subject (typically a human) but can also detect decreases. For example, some sample components, particularly antibodies, can be detected to decrease in a test sample, such as a disease or vaccinated sample or any other of the samples types mentioned, and other sample components increase.

Quality Control Indicators.

The quality of an array on the invention can be determined based on an analysis of two independent factors: 1) the consistency of fluorescence signal between corresponding features in multiple arrays; and 2) the similarity of the distribution of fluorescence signals measured over the population of features. Surprisingly, an analysis of these two partially independent factors suffices to determine if an immunosignaturing array is of an acceptable quality. To better illustrate how these two factors can be applied to a quality control analysis consider the following:

The correspondence of the binding intensities of different peptide features in multiple, identical arrays that have been used to analyze samples from different subjects share a degree of similarity. The level of correspondence can be measured statistically, for example with a Pearson Correlation or as a coefficient of variance. The Pearson Correlation between array data that is sufficiently similar may be at least 0.7, at least 0.8, at least 0.9, at least 0.95 or at least 0.99. The correspondence between binding intensities of corresponding features in a set of arrays can be detected with fluorescence imaging techniques. To illustrate the concept, in any given human population, the height of an adult human is a trait that should fall within expected ranges, e.g. between about 4 feet to about 7 feet. If one were to measure the same people twice, one would expect that the same people that were measured as being tall the first time would also be tall in the second measurement. If this is not the case, one would expect that the measurement was faulty. A correlation of detected binding intensities from the arrays can indicate if an array contains a desired degree of binding intensity similarity. If a desired degree of similarity exists, the array has met one quality control threshold. If the desired degree of similarity does not exist, the array has not met a quality control threshold.

In addition, it is possible to measure the shape of the overall distribution of binding intensities from many different arrays and determine how similar they are. These binding distributions can be detected with fluorescence imaging techniques by measuring fluorescence from a dye conjugated to a probe molecule. To illustrate the concept, in any given human population, the height of an adult human is a trait that should fall within expected ranges, e.g. between about 4 feet to about 7 feet. However, the distribution of heights is not even over this range; there are very few adults that are 4 feet in height and very few that are 7 feet. One would expect to always find more or less the same distribution if one is randomly selecting people from the population and measuring their height. If one does not find a similar distribution, one might suspect that the measurement was faulty. Detection of a binding intensity that corresponds to a known trait suggests that the array has met one quality control threshold. Absence of such binding suggests that the array has not met one quality control threshold.

In some embodiments, a quality control analysis of an array of the invention comprises: a) detecting a binding intensity of a sample to a plurality of features on a peptide array; b) determining a binding intensity of the sample to each feature on the array; and c) statistically correlating the binding intensities of each feature.

Derivative Analyses

In addition to being useful in themselves for analyses of samples as discussed above, the present methods are also useful for determining derivative compounds and detection devices. In a simple form of such methods, a derivative device or other array in constructed containing one or more compounds known to be associated with a given disease, susceptibility to disease or other condition described above, and omission of other compounds from the primary array not found to be informative for this disease, susceptibility or other condition. In some such methods, only a small proportion of the compounds used in a primary array (e.g., less than 0.1%, 1% or 5% are retained). In other methods, a component of the sample bound by some of the compounds in a primary array is identified by any of the approaches discussed in the previous section. Having identified a component of the sample, one or more known binding partners of the component are also identified. The known binding partners can be compounds from the primary array, antibodies to the component or other compound, such as a synbody that is known to bind to the component. The known binding partner(s) can then be used to detect the sample component to which they are known to being by any otherwise conventional diagnostic assay. For example, if the known binding partner is an antibody, the assay can be an ELISA, immunoprecipitation, radioimmunoassay or the like. If a plurality of known binding partners are used, the known binding partners can be immobilized in an array format. The known binding partners can also be incorporated into diagnostic kits or diagnostic device (e.g., attached to a support). Such arrays, diagnostic devices and kits can be manufactured by conventional means. Of course, once the known binding partners of a component have been identified, it is not necessary to repeat the initial screening with the primary array for subsequent manufacture of such arrays, diagnostic devices and kits.

Although the embodiments have been described with reference to the presently preferred embodiments, various modifications can be made without departing from the invention. Unless otherwise apparent from the context any step, element, embodiment, feature or aspect of the embodiments can be used with any other.

EXAMPLES

Example 1: Overall Correlation Coefficient Assessment

Arrays of peptides were fabricated by in situ synthesis such that there were 330,000 peptides in each array. Twelve such arrays were subjected to immunosignaturing with six different kinds of samples. In 6 of these samples, one secondary antibody for IgM was used. In 6 of these samples, a different secondary antibody for IgG was used. Using an IgG secondary antibody accidentally instead of an IgM secondary could represent an "error" in the assay condition that would alter the overall pattern of binding observed.

Correlation coefficients were determined between all possible pairs of arrays (Pearson Correlation). The average correlation coefficient between the samples that used the IgM secondary antibody was 0.92+/−0.02 (these numbers represent that average and the standard deviation, SD). The correlation coefficient between IgM and IgG samples on average was 0.59+/−0.06. Each of the individual samples that "mistakenly" used IgG had correlation values in comparison with the IgM correct assay that differed by a statistically significant margin. It clearly would have been possible to detect the use of the "wrong" secondary antibody had one array been treated incorrectly relative to the others by this method.

Accordingly, a failed process may be indicated if the correlation coefficient between a given assay and a standard assay is greater than a threshold value. In some embodiments the threshold value may be defined as a percentage of the correlation coefficient between assays that were done correctly. In this case, to pass QC, the threshold percentage should be at least under 3%, at least under 4%, at least under 5%, at least under 6%, at least under 7%, at least under 8%, at least under 9%, at least under 10%, at least under 15%, at least under 20%, at least under 25%, at least under 30%, at least under 35%, at least under 40%, at least under 45%, or at least under 50%.

Alternatively, in some embodiments the threshold value may be defined in terms of the standard deviation (SD) derived from generating many correlation coefficients between assays that were done correctly and a standard assay. In this case, to pass QC, the threshold correlation coefficient between a given assay and the standard assay should be at least under 2×SD, under 2.5×SD, under 3×SD, under 3.5×SD or under 4×SD.

Example 2: Relating Array Binding Intensity Pattern to Fabrication Sequence

An array of peptides, with known peptide sequences, was generated by a mask-based, in situ synthetic process on a silicon oxide surface. Each step in the process consisted of the removal of a blocking group from the end of a subset of the growing peptides and addition of a specific amino acid only to those positions until the desired peptide length was achieved.

The peptide array was then exposed to a sample of human serum and the IgG bound was quantified by addition of a labeled secondary antibody and visualized. The synthesis of the array deliberately left out the first half of the masks (i.e., those steps were not performed), simulating failed steps in the synthesis (masks 1-69). Masks 70-140 were used properly to synthesize, and subsequently lengthen, peptides on the array.

The average intensity values measured for the subset of peptides only that should have been modified by each of the synthesis steps above, including synthesis where no masks were used (i.e., simulating that the steps were not performed) were subsequently determined and plotted against each synthesis step. The resulting average values are shown in FIG. 1. As can be seen from FIG. 1, steps in which the synthesis did not occur, i.e. masks 1-69 where no amino acids were added to the peptide fragment on the array, resulted in a similar, universal average value. This is in stark contrast to the average intensity values obtained for the subset of peptides affected with masks 70-140, where a statistically unique value of binding was obtained for these synthesis steps. This statistically unique pattern of binding for each synthesis step, which corresponds with successful synthesis of the peptides on the array, is largely reproducible across different batches of arrays with the same peptide sequences. In our experience, a unique pattern of binding can be obtained for each synthesis steps that differs by a threshold percentage when compared, for example, to a universal average intensity value.

This universal average intensity value can be obtained, for example, by averaging all of the peptides (e.g., all 330,000 peptides) on the array after synthesis occurs. Other means can be used for obtaining this universal average intensity value, including but not limited to averaging all peptides on the array after each synthesis step and averaging the values of those numbers obtained.

An average intensity value at a given synthesis step which does not significantly differ from this universal average intensity value may indicate the failure of synthesis, i.e. addition of an amino acid, at that step. A failed synthesis step may be indicated if the difference between the average intensity value at a given step and the universal average intensity value is not above a threshold percentage of about 2%, of about 5%, or about 10%, or about 15%, or about 20%, or about 25%, or about 30%, or about 35% or about 40%, or about 45%, or about 50%. The threshold average intensity value difference in some embodiments should be at least over 2%, at least over 3%, at least over 4%, at least over 5%, at least over 6%, at least over 7%, at least over 8%, at least over 9%, at least over 10%, at least over 15%, at least over 20%, at least over 25%, at least over 30%, at least over 35%, at least over 40%, at least over 45%, or at least over 50%.

Alternatively, a failed synthesis step may be indicated if the difference between the average intensity value at a given step and the universal average intensity value is not above a threshold defined in terms of the standard error (SE) determined for the given step's average intensity. In some embodiments, a failed synthesis step is indicated if the difference between the average intensity value at a given synthesis step and the universal average intensity value is less than 2×SE, less than 2.5×SE, less than 3×SE, less than 3.5×SE or less than 4×SE. In some embodiments, the threshold difference should be at least over 2×SE, at least over 2.5×SE, at least over 3×SE, at least over 3.5×SE or at least over 4×SE.

This pattern of effect is largely reproducible even when different diseases are considered, because the vast majority of the binding signals from the peptides are not strongly affected (at least relative to the average). Accordingly, in other embodiments, the determination of whether a synthesis step may have failed can be run concurrently with subject samples as a primary or additional means of quality control of the peptide array. Alternatively, this quality control method can also be run on single peptide arrays produced in a batch run, either as a primary or additional means of quality control of the peptide array.

Example 3: Relating Array Binding Intensity Pattern to Fabrication Sequence

Another way of averaging the data and determining if an amino acid addition step may have failed during synthesis, is based on the position and the monomer added. This may be distinct from the step of the synthesis if a particular step adds a particular monomer at different positions within a peptide.

The example shown in Table 1 is for a peptide array produced on a surface. The peptide array consisted of 330,000 peptides. The peptide array was exposed to a sample of human serum as above, and the IgG bound to the array from the sample was detected with labeled secondary antibody and visualized. The average value of the intensity of IgG binding to each peptide that had a particular monomer at a particular position is determined relative to the average intensity over the whole array (i.e. all 330,000 peptides), to obtain a relative value of IgG binding to a particular monomer to a particular position. A matrix of position and amino acid was generated. Note that the way the peptides were made, not all amino acids are present in all positions and thus there is a blank at position A-13 in the matrix.

One can see that there are considerable variations in average values of intensity across the matrix because the particular amino acids and positions have different effects on binding. To determine if the variations in average values of intensity are due to positional effects of particular amino acids, the data was re-analyzed without knowledge of the particular amino acids and positions. Table 2 is from exactly the same array as in Table 1, except that the data was scrambled such that the correlation between a particular intensity value and a particular peptide in the array was randomly changed. Note that almost all of the positions and amino acids now take on the average value of intensity (i.e., everything is normalized to that average value which is considered 1.0 for this example). Those positions/amino acids near the edge that show some variation from average do so because the number of peptides with that amino acid at that position is small.

TABLE 1

Table 1. Intensity changes for peptide subsets relative to global average. The subset of peptides averaged for each value corresponds to peptides with the particular amino acid (y-axis) and particular position in the peptide (x-axis)

|     | 1 | 2 | 3 | 4 | 5 | 6 | 7 | 8 | 9 | 10 | 11 | 12 | 13 |
|-----|---|---|---|---|---|---|---|---|---|----|----|----|----|
| A | 0.88 | 0.91 | 0.96 | 1.00 | 1.05 | 1.08 | 1.09 | 0.98 | 0.76 | 0.85 | 1.06 | 0.83 | |
| D | 0.88 | 0.96 | 1.01 | 1.12 | 1.15 | 1.16 | 1.15 | 1.15 | 1.15 | 1.13 | 1.12 | 1.12 | 1.11 |
| E | 0.98 | 1.09 | 1.17 | 1.16 | 1.16 | 1.15 | 1.16 | 1.16 | 1.15 | 1.14 | 1.12 | 1.13 | 1.12 |
| F | 0.77 | 0.86 | 0.91 | 0.85 | 0.82 | 0.84 | 0.83 | 0.83 | 0.83 | 0.83 | 0.83 | 0.83 | 0.85 |
| G | 1.17 | 1.02 | 1.08 | 1.07 | 1.08 | 1.07 | 1.09 | 1.10 | 1.12 | 1.12 | 1.10 | 1.10 | 0.99 |
| H | 1.09 | 1.05 | 1.09 | 1.07 | 1.07 | 1.07 | 1.11 | 1.17 | 1.23 | 1.23 | 1.23 | 1.30 | 1.23 |
| K | 0.92 | 0.94 | 0.94 | 0.93 | 0.95 | 0.92 | 0.93 | 0.92 | 0.94 | 0.93 | 0.90 | 0.92 | 0.95 |
| L | 0.90 | 0.78 | 0.81 | 0.82 | 0.83 | 0.82 | 0.80 | 0.81 | 0.84 | 0.85 | 0.87 | 0.91 | 0.88 |
| N | 0.91 | 0.92 | 0.95 | 0.91 | 0.91 | 0.90 | 0.90 | 0.91 | 0.93 | 0.93 | 0.93 | 0.97 | 0.99 |
| P | 1.48 | 1.22 | 1.21 | 1.18 | 1.18 | 1.18 | 1.16 | 1.16 | 1.16 | 1.16 | 1.13 | 1.12 | 1.16 |
| Q | 0.99 | 1.00 | 1.01 | 0.96 | 0.94 | 0.94 | 0.92 | 0.92 | 0.91 | 0.91 | 0.90 | 0.89 | 0.85 |
| R | 0.97 | 0.93 | 0.96 | 0.99 | 1.00 | 1.00 | 1.00 | 1.02 | 1.05 | 1.05 | 1.04 | 1.10 | 1.07 |
| S | 0.93 | 0.84 | 0.89 | 0.91 | 0.92 | 0.91 | 0.92 | 0.94 | 0.97 | 0.98 | 0.98 | 0.99 | 1.03 |
| V | 0.95 | 0.92 | 0.92 | 0.92 | 0.93 | 0.93 | 0.95 | 0.95 | 0.97 | 0.95 | 0.94 | 0.93 | 0.95 |
| W | 1.31 | 1.71 | 1.21 | 1.24 | 1.17 | 1.22 | 1.19 | 1.17 | 1.17 | 1.13 | 1.08 | 1.06 | 1.03 |
| Y | 0.88 | 0.86 | 0.88 | 0.87 | 0.84 | 0.82 | 0.81 | 0.81 | 0.81 | 0.81 | 0.79 | 0.81 | 0.78 |
| SD | 0.18 | 0.22 | 0.12 | 0.13 | 0.12 | 0.13 | 0.13 | 0.14 | 0.15 | 0.14 | 0.13 | 0.14 | 0.13 |
| ave | 1 | 1 | 1 | 1 | 1 | 1 | 1 | 1 | 1 | 1 | 1 | 1 | 1 |

TABLE 2

Table 2. Same as Table 1 except that the assignment of peptides to the list of intensity values was scrambled. Note that the number of peptides in each subset averaged is smaller on the top and right edges and thus there is greater variance.

|     | 1 | 2 | 3 | 4 | 5 | 6 | 7 | 8 | 9 | 10 | 11 | 12 | 13 |
|-----|---|---|---|---|---|---|---|---|---|----|----|----|----|
| A | 1.00 | 1.00 | 1.00 | 1.00 | 1.00 | 0.99 | 0.98 | 0.99 | 0.88 | 1.00 | 0.95 | 1.09 | |
| D | 1.01 | 1.00 | 1.00 | 1.00 | 0.99 | 1.00 | 1.01 | 1.00 | 1.00 | 1.00 | 1.00 | 1.00 | 0.99 |
| E | 0.99 | 1.00 | 0.99 | 0.99 | 1.00 | 1.00 | 1.00 | 1.00 | 1.00 | 1.00 | 1.00 | 1.00 | 1.03 |
| F | 1.00 | 1.00 | 0.99 | 0.99 | 1.02 | 1.01 | 1.00 | 1.00 | 1.01 | 0.99 | 1.00 | 0.98 | 0.95 |
| G | 1.00 | 1.00 | 1.00 | 1.00 | 1.00 | 1.00 | 1.01 | 1.00 | 1.01 | 1.00 | 0.99 | 1.00 | 0.90 |
| H | 1.00 | 1.00 | 0.99 | 1.00 | 1.00 | 1.00 | 1.00 | 1.00 | 1.02 | 1.00 | 1.01 | 1.02 | 1.00 |

TABLE 2-continued

Table 2. Same as Table 1 except that the assignment of peptides to the list of intensity values was scrambled. Note that the number of peptides in each subset averaged is smaller on the top and right edges and thus there is greater variance.

|     | 1    | 2    | 3    | 4    | 5    | 6    | 7    | 8    | 9    | 10   | 11   | 12   | 13   |
|-----|------|------|------|------|------|------|------|------|------|------|------|------|------|
| K   | 0.99 | 1.01 | 1.00 | 1.00 | 1.00 | 1.00 | 1.00 | 0.99 | 1.01 | 0.99 | 1.00 | 1.00 | 1.01 |
| L   | 1.01 | 1.01 | 1.00 | 1.01 | 1.00 | 1.00 | 1.00 | 1.00 | 1.02 | 1.00 | 0.98 | 0.99 | 1.02 |
| N   | 1.00 | 1.00 | 1.00 | 1.01 | 1.00 | 1.00 | 1.00 | 1.00 | 1.00 | 1.00 | 0.97 | 0.97 | 0.99 |
| P   | 1.00 | 0.99 | 1.01 | 0.99 | 1.00 | 1.00 | 1.01 | 0.99 | 1.01 | 1.01 | 1.03 | 1.02 | 1.04 |
| Q   | 1.00 | 1.00 | 0.99 | 1.00 | 1.01 | 1.00 | 1.01 | 1.00 | 1.01 | 1.02 | 1.02 | 0.96 | 1.02 |
| R   | 0.99 | 1.00 | 1.00 | 1.00 | 1.00 | 0.99 | 1.00 | 1.00 | 1.00 | 0.98 | 1.00 | 0.99 | 0.99 |
| S   | 0.99 | 1.00 | 1.00 | 1.00 | 0.99 | 1.00 | 1.00 | 1.01 | 1.01 | 1.01 | 1.01 | 1.01 | 0.94 |
| V   | 1.00 | 0.99 | 1.00 | 1.00 | 1.00 | 1.00 | 1.01 | 1.00 | 1.01 | 1.00 | 1.00 | 0.99 | 1.04 |
| W   | 1.00 | 0.99 | 1.03 | 1.01 | 1.00 | 1.00 | 1.00 | 1.01 | 1.01 | 1.00 | 1.01 | 1.00 | 1.05 |
| Y   | 1.01 | 1.00 | 1.01 | 1.00 | 0.99 | 1.00 | 1.00 | 1.00 | 1.00 | 1.00 | 1.01 | 1.00 | 1.04 |
| SD  | 0.01 | 0.01 | 0.01 | 0.01 | 0.01 | 0.00 | 0.01 | 0.01 | 0.03 | 0.01 | 0.02 | 0.03 | 0.04 |
| ave | 1    | 1    | 1    | 1    | 1    | 1    | 1    | 1    | 1    | 1    | 1    | 1    | 1    |

As above, the universal average intensity value can also be obtained, for example, by averaging all peptides on the array after each synthesis step and averaging the values of those numbers obtained.

A relative intensity value for an amino acid at a particular position on a peptide may indicate the failure of synthesis, i.e. addition of an amino acid, where the synthesis step occurred. A failed synthesis step may be indicated if the relatively intensity value obtained is not above the universal average intensity value (i.e. 1.0) by a threshold percentage of about 2% or about 5%, or about 10%, or about 15%, or about 20%, or about 25%, or about 30%, or about 35% or about 40%, or about 45%, or about 50%. The threshold average intensity value difference in some embodiments should be at least over 2%, at least over 3%, at least over 4%, at least over 5%, at least over 6%, at least over 7%, at least over 8%, at least over 9%, at least over 10%, at least over 15%, at least over 20%, at least over 25%, at least over 30%, at least over 35%, at least over 40%, at least over 45%, or at least over 50%.

Alternatively, a failed synthesis step may be indicated if the relatively intensity value obtained is not above the universal average intensity value (i.e. 1.0) by a threshold defined in terms of the standard error (SE) determined for the relative intensity value. In some embodiments, a failed synthesis step is indicated if the difference between the average intensity value at a particular position for a given amino acid and the universal average intensity value is less than 2×SE, less than 2.5×SE, less than 3×SE, less than 3.5×SE or less than 4×SE. In some embodiments, the threshold difference should be at least over 2×SE, at least over 2.5× SE, at least over 3×SE, at least over 3.5×SE or at least over 4×SE.

As above, the determination of whether a synthesis step may have failed can be run concurrently with subject samples as a primary or additional means of quality control of the peptide array. Alternatively, this quality control method can also be run on single peptide arrays produced in a batch run, either as a primary or additional means of quality control of the peptide array.

While preferred embodiments have been shown and described herein, it will be obvious to those skilled in the art that such embodiments are provided by way of example only. Numerous variations, changes, and substitutions will now occur to those skilled in the art without departing from the embodiments. It should be understood that various alternatives to the embodiments described herein may be employed in practicing the described methods. It is intended that the following claims define the scope of the embodiments and that methods and structures within the scope of these claims and their equivalents be covered thereby.

Example 4: Analytic Framework for Quality Control (QC) Analysis

We describe herein an analytic framework that has been utilized in determining the quality and integrity of an array of the invention.

An array of the invention was synthesized with ~350,000 features on a composite silicon crystal/silicon oxide wafer. The silicon oxide layer is directly functionalized with linker groups suitable for peptide synthesis. Manufactured arrays with peptides were incubated with a test antibody. This antibody is detected with an anti-idiotype, anti-species secondary antibody with a fluorescent tag. The wafers were scanned and converted to numerical values by applying a virtual grid over the image and calculating the measured intensities for each of the ~350,000 peptides. This process creates a 'gpr' file containing a list of the intensities for each peptide, and the relative location of the peptides in the image. This text file containing the numerical representation of the array image is then used for subsequent numerical analysis. In the present example, an Innopsys Innoscan 910AL 2-color laser scanner is used for acquiring the image, and the same acquisition software is also used to automatically grid and convert the images. Any laser scanner with 1.0 micron resolution, 550 nm and 650 nm lasers, and high discrimination emission filter is capable of scanning peptide arrays synthesized on opaque and partially reflective silicon/silicon oxide surfaces. Images and gpr files are stored in a fileserver until needed.

Each gpr file contains specific columns representing aspects of the translated image. One of the columns is denoted "Median Foreground XXXnm" column. "XXXnm" corresponds to the wavelength of the fluorophore linked to the detection antibody. In this example, multiple wavelengths were detected simultaneously, as multiple isotypes can be detected using the two colors that the scanner can detect. More than one antibody with distinct isotypes, such as IgG and IgM, can be used in a quality control analysis.

Gpr files are read into R, a free-ware 64-bit analytical/statistical programming language (CRAN.org). A matrix is created from the Median Foreground column, with each row given a unique peptide name, and each column given a unique sample name. No peptide or sample averaging is performed.

The content within this matrix represents the data of interest for the quality control analysis. Each quality control analysis can be performed on arrays from multiple wafers. Table 3 illustrates the parameters considered by a computer program product in performing a quality control analysis of an array.

TABLE 3

```
sortArray_QC <-
# sortArray_QC( ) rank orders immunosignaturing arrays by similarity# QC <-
sortArray_QC(FG,arraylimit=10,pepsmpl=20,cor.scale=0.2,ks.scale)
# ARGUMENTS:
#FG: numeric matrix of foreground spot intensities from an immunosignaturing
#array, with peptide features in rows and arrays in columns.
#arraylimit: integer; minimum number of arrays to compare-- the stopping point for the
algorithm.
#pepsmpl: integer; fraction of peptides to sample, where 20 means every 20th; pepsmpl=1 will
use the entire set.
#cor.scale: number; correlation scaling factor for calculating distance; default value is
0.20.
#ks.scale: number; scaling factor to apply to mean KS p-values when calculating the QC
distance. If omitted, it will be calculated as: max(mean.ks) – mean(mean.ks), 1st iteration
# VALUE; returns a data.frame with rownames taken from the column names of FG, ordered by
the rank column, and columns:
#rank: rank order of the arrays, from best (1) to worst (2)
#mean.cor: mean Pearson correlation to arrays with lower rank values
#mean.ks: mean log10(p-value), KS test of distribution, to arrays with lower rank values
#qc.dist: the distance calculated from scaled mean.cor and mean.ks
```

Fluorescence values, sample name, peptide number and peptide sequence enter the QC program. Values returned from the analysis are linear, unscaled distances that integrated two orthogonal measures of consistency and reproducibility. First, the Kolmogorov-Schmirnov goodness of fit (ks.gof) value represents a measure of the similarity of the data distribution between two arrays of data. Second, Pearson's Correlation Coefficient (cor) represents the linear relatedness between two arrays of data. The distance value is a representation of a near-even weighting of the average of these assessments across all tested arrays. This means every possible comparison across any number of arrays is performed, and the average for these samples is returned. A fixed cutoff of 0.70 avg. correlation and a value of <2.5 for the avg.$-\log_{10}$ KS-GOF score was used in evaluating a threshold quality level for the wafers.

A non-reported value was also calculated, to be used as a checksum that ensures the scores calculated above represent authentic, reproducible, expected data and convey array performance. After the acceptable ks.gov and cor values were determined, the coefficient of variation (CV, stdev/mean) is calculated for each peptide across the samples being tested. The average CV for each array is computed and assigned to a vector. As the QC process iterates, files that did not meet the aforementioned minimum threshold were discarded iteratively. Each iteration discards arrays that failed to meet the minimum threshold for reproducibility. Each iteration, the average CV per array is calculated. As files that do not meet the minimum quality control threshold were removed from the list, the average CV across the remaining arrays should decrease, indicating that the program is removing the files that had the worst reproducibility. The CV values are stored in a vector.

CV's are expected to somewhat vary from synthesis-to-synthesis. However, if a downward trend in CV is not observed in the analysis framework described above, the original data should be independently examined for possible image artifacts or biases not detectable by the KS-GOF/Correlation calculation. This set of CV values can then be analyzed using a Kolmogorov complexity (KC) calculation.

If the KC value exceeds KC>0.49, the images should be examined for systematic bias or image artifacts, or other parts of the image acquisition, gridding, or alignment process should be considered suspect.

As analysis and manufacturing changes are implemented, it may be necessary to revisit the minimum threshold values currently used to determine the fabrication of an array of acceptable quality. In the experiment described herein, the threshold cutoff was decided empirically through multiple rounds of testing immunosignatures that correspond to various disease states, various arrays, and various monoclonal antibodies. The cutoff is presently near the range of human to human variability, ensuring that the technical variability does not exceed the biological variability.

Example 5: Analytical Analysis Performed after Quality Control of Acceptable Files Once an array is found to conform to the Quality Control standards specified in Example 4, further quality control analysis can be performed using the following framework. This framework analysis can be applied to selection/training, sample prediction of unknowns, leave-out cross-validation, or holdout validation. Selection is the process by which peptides are selected to give the best prediction of disease in a well-defined cohort and only in that cohort. Should the cohort be 1 disease vs. healthy, the selection process is limited to only detecting that disease against healthy persons. Should the cohort be 1 disease vs. non-disease, the selection process now encompasses non-healthy but non-disease 1 samples. Sample prediction of unknowns is the process by which the selection/training process is validated. If the training process was robust, any disease that was never used in the training process, and is blinded to the analyst, should be detected and classified as the disease at high accuracy. This test process enables one to ensure the training process is adequate or needs to be expanded. Leave-out cross-validation is used when blinded samples are unavailable. Cross-validation removes (typically) 1 sample from the dataset, which is then used as the test data. This process of removing and testing samples is done repeatedly until every sample was tested once. Holdout is a process of removing a fixed percentage of samples from the training process, and then using them as test samples. This is nearly identical to a blinded train/test trial, other than the holdout samples are known to the analyst. There is no mathematical difference between blinded trials and holdout trials.

The following example describes further steps taken in the quality control analysis of the array described in Example 4.

Figure 2:
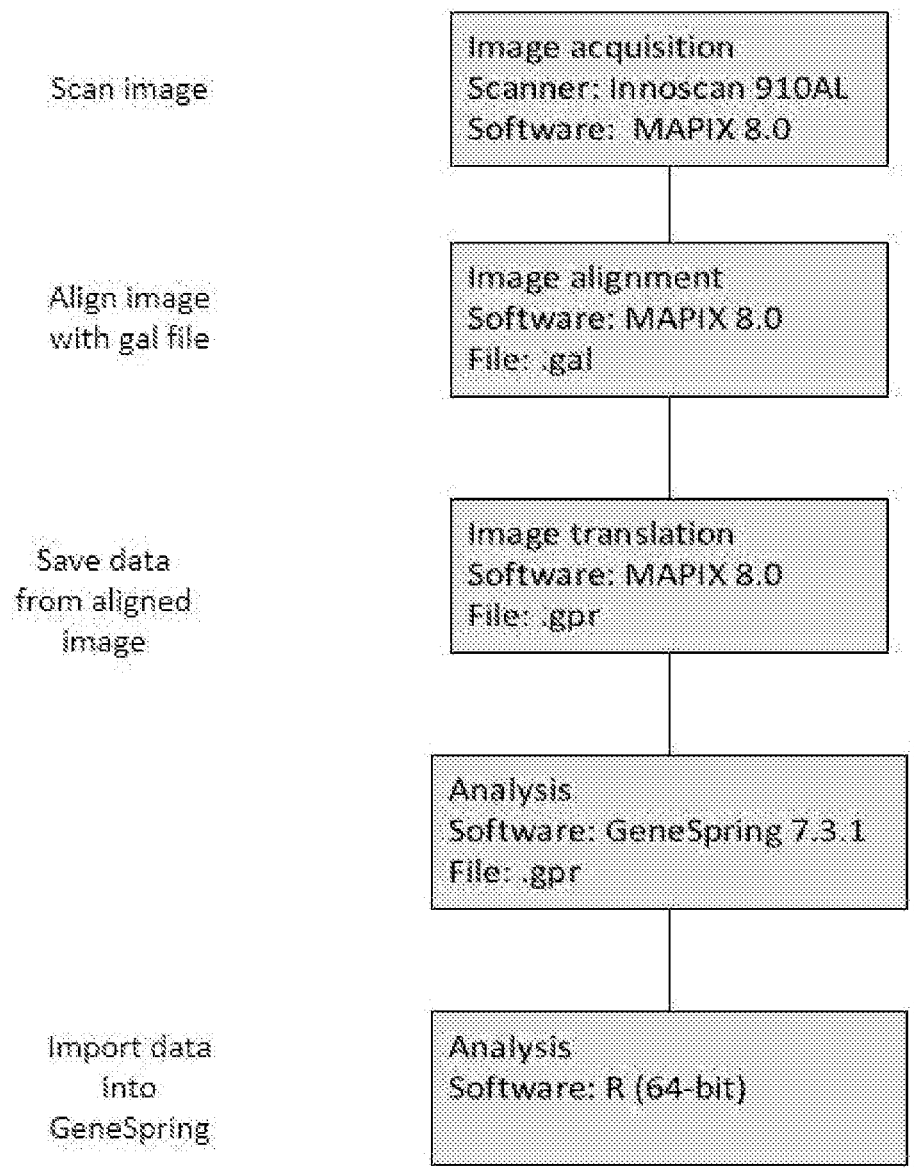
FIG. 2 flowchart illustrating actors and processes used in image acquisition, alignment, translation, and analysis.

Each gpr file can be loaded into GeneSpring 7.3.1 (subsequently referred to as GS, currently sold by Agilent Technologies, Santa Clara, Calif.). GS creates a matrix of columns from the gpr files. One column corresponds to all ~350,000 peptides and 1 sample. In this example, a matrix was created in GS that listed each peptide in the array in a row and the sample analyzed in a column. In the current example, QC analysis, values for each gpr file of each identical peptide were averaged. Values less than 0.01 were converted to 0.01. FIG. 2 is a flowchart illustrating actors and processes used in the image acquisition, alignment, translation, and analysis described herein.

The overall fluorescence signal was measured and the median signal for each of the ~350,000 peptides in the array was taken from the gpr file. The value measured for each feature was divided by the median value that was calculated.

Subsequently, the median signal for each of the 350,000 peptides and each sample being analyzed was calculated. Each value from each array for a given peptide was divided by the median signal for that peptide.

Samples were assigned attributes. Attributes included 'disease', 'technical replicate', 'biological replicate', 'wafer', 'assay', etc. The attributes were used to average replicates; identically-named samples (technical replicates) were averaged for further analysis.

Each disease that was analyzed was assigned a disease class. Disease classes were in turn used for subsequent feature selection.

1) Feature selection: Once attributes were assigned and averages were defined, the feature selection process began. The number of disease classes was defined by the attributes.

2) Statistical analysis: For a two-class analysis, feature-selection was performed by t-test between the two samples, then pattern matching. T-test is a Welch-corrected t-test with multiple testing accounted for by setting Family Wise Error Rate to 5% (FWER=5%), reducing false positives to 5% of the total features selected. Pattern matching was performed in GS by selecting a pattern of expression. The selected pattern was defined as consistently high for class 1 and consistently low for class 2 using Pearson's Correlation coefficient as the metric to judge the goodness of fit to the selected pattern.

In the analysis described in this example, twenty-five peptides were selected from the t-test pre-filtered list that survived the pattern matching analysis. The High/Low pattern is then reversed and twenty-five more peptides are selected. Fifty peptides were used for two-class prediction.

For multi-class analysis, feature selection was performed by Type I Fixed-Effects ANOVA with setting Family Wise Error Rate to 5% (FWER=5%). Pattern matching was done as described in the statistical analysis 2), but for each class, a pattern of UP for that class, and a pattern of DOWN for all other classes was determined with 50 total peptides selected for each class.

3) Classification: For experiments analyzing only 2 classes, LDA, kNN, NB and SVM classifiers were determined with Leave One Out Cross-Validation. Error for each classifier was provided. For experiments using multiple classes, the LDA was not used due to propensity to error due to colinearity affects. In the analysis described in this example, the false positive rate was equal to false negative rate.

Within classification, a resampling could be performed given a sufficient sample size. Resampling is a process by which samples are randomly selected to serve as "training" and "test" at a predefined ratio. A suitable resampling ration is a 4:1 ratio of training to test.

4) Validation: either a permuted t-test or permuted ANOVA could be performed to ensure that there were no group labels that produced lower p-values than the correct assignments. With 350,000 peptides, poor reproducibility can yield situations where p-values are not in the $10^{-8}$ to $10^{-30}$ range deemed acceptable for an array of the invention.

5) Charting and reports: a classification error was reported as FP, FN, TP, TN rates, NPV, PPV, sensitivity, specificity, and harmonic mean. Charts included 2 dimensional hierarchical clustering using Euclidean distance, Pearson's correlation, or other metric, specifically using average linkage as the metric for creating dendromer linkages (heatmaps).

PCA charts can provide relative class separation in graphical format. ROC curves can be provided as charts when desired/needed using pROC library in S+.

Example 6: Computer Architectures

Figure 3:
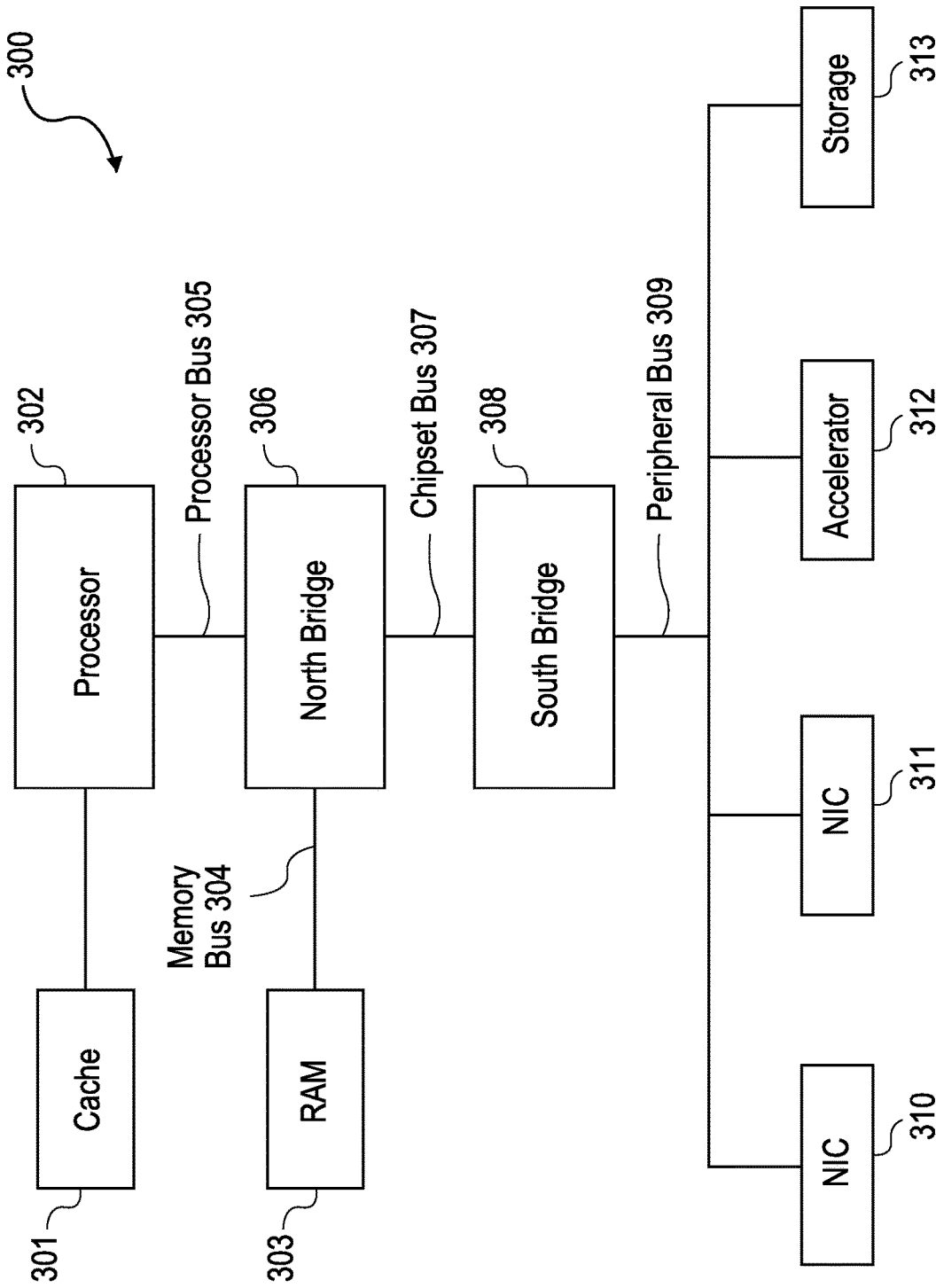
FIG. 3 is a block diagram illustrating a first-example architecture of a computer system that can be used in connection with example embodiments of the present invention.

Various computer architectures are suitable for use with the invention. FIG. 3 is a block diagram illustrating a first example architecture of a computer system 300 that can be used in connection with example embodiments of the present invention. As depicted in FIG. 3, the example computer system can include a processor 302 for processing instructions. Non-limiting examples of processors include: Intel Core i7™ processor, Intel Core i5™ processor, Intel Core i3™ processor, Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can be used, whether in a single computer system, in a cluster, or distributed across systems over a network comprising a plurality of computers, cell phones, and/or personal data assistant devices.

Data acquisition, processing and storage.

As illustrated in FIG. 3, a high speed cache 301 can be connected to, or incorporated in, the processor 302 to provide a high speed memory for instructions or data that have been recently, or are frequently, used by processor 302. The processor 302 is connected to a north bridge 306 by a processor bus 305. The north bridge 306 is connected to random access memory (RAM) 303 by a memory bus 304 and manages access to the RAM 303 by the processor 302. The north bridge 306 is also connected to a south bridge 308 by a chipset bus 307. The south bridge 308 is, in turn, connected to a peripheral bus 309. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 309. In some architectures, the functionality of the north bridge can be incorporated into the processor instead of using a separate north bridge chip.

In some embodiments, system 300 can include an accelerator card 312 attached to the peripheral bus 309. The accelerator can include field programmable gate arrays (FPGAs) or other hardware for accelerating certain processing.

Software Interface(s).

Software and data are stored in external storage 313 and can be loaded into RAM 303 and/or cache 301 for use by the processor. The system 300 includes an operating system for managing system resources; non-limiting examples of operating systems include: Linux, Windows™, MACOS™, BlackBerry OS™, iOS™, and other functionally-equivalent operating systems, as well as application software running on top of the operating system.

In this example, system 300 also includes network interface cards (NICs) 310 and 311 connected to the peripheral bus for providing network interfaces to external storage, such as Network Attached Storage (NAS) and other computer systems that can be used for distributed parallel processing.

Computer Systems.

Figure 4:
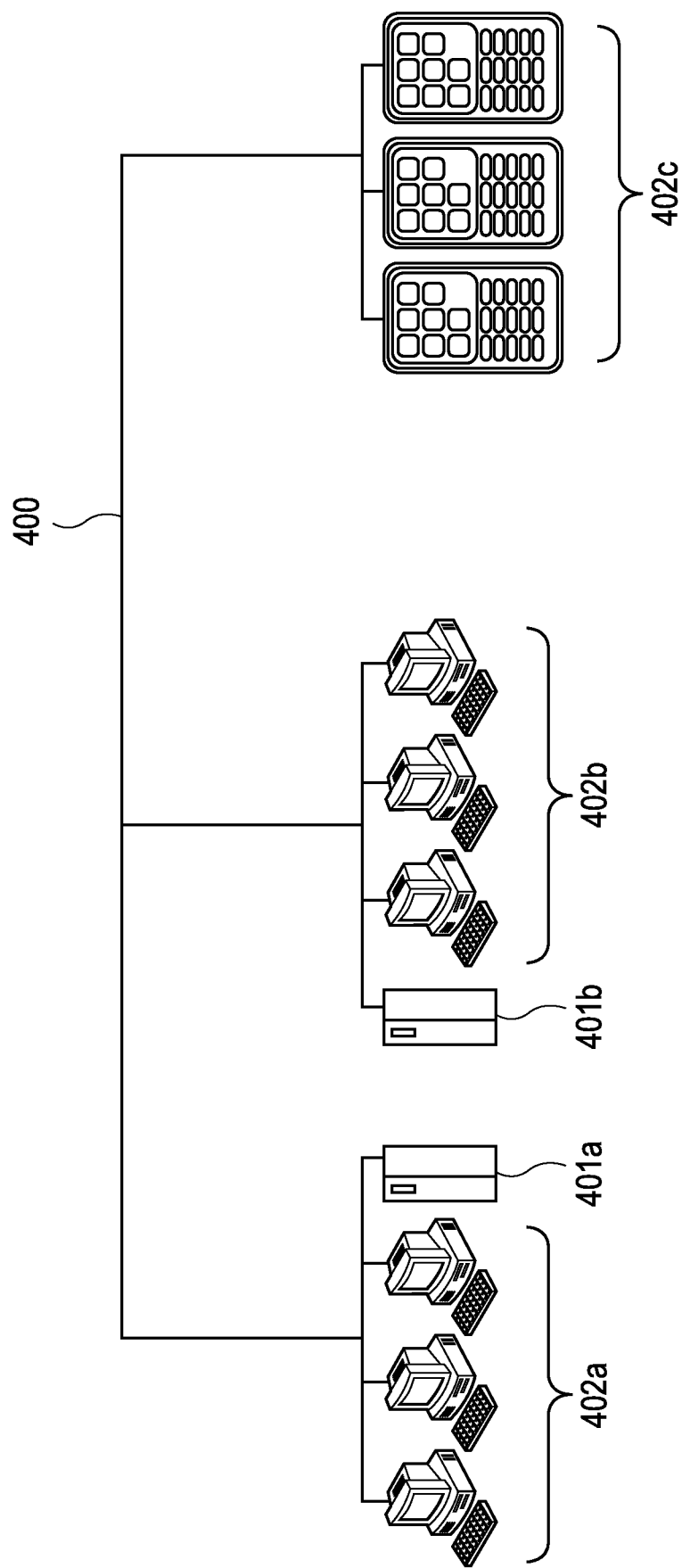
FIG. 4 is a diagram illustrating a computer network that can be used in connection with example embodiments of the present invention.

FIG. 4 is a diagram showing a network 400 with a plurality of computer systems 402a, and 402b, a plurality of cell phones and personal data assistants 402c, and Network Attached Storage (NAS) 401a, and 401b. In some embodiments, systems 402a, 402b, and 402c can manage data storage and optimize data access for data stored in Network Attached Storage (NAS) 401a and 402b. A mathematical model can be used for the data and be evaluated using distributed parallel processing across computer systems 402a, and 402b, and cell phone and personal data assistant systems 402c. Computer systems 402a, and 402b, and cell phone and personal data assistant systems 402c can also provide parallel processing for adaptive data restructuring of the data stored in Network Attached Storage (NAS) 401a and 401b. FIG. 4 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some embodiments, processors can maintain separate memory spaces and transmit data through network interfaces, back plane, or other connectors for parallel processing by other processors. In some embodiments, some or all of the processors can use a shared virtual address memory space.

Virtual Systems.

Figure 5:
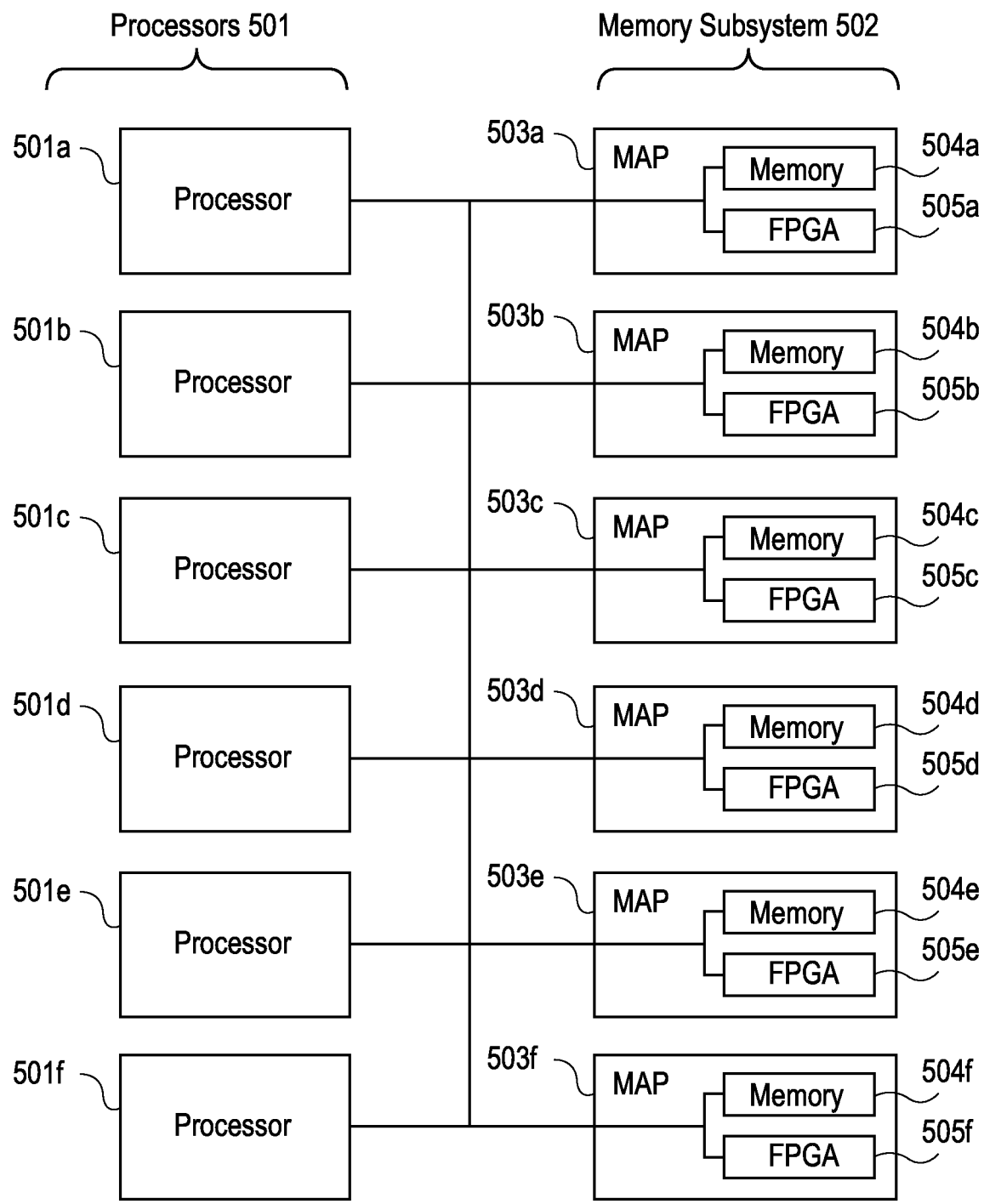
FIG. 5 is a block diagram illustrating a second example architecture of a computer system that can be used in connection with example embodiments of the present invention.

FIG. 5 is a block diagram of a multiprocessor computer system using a shared virtual address memory space. The system includes a plurality of processors 501a-f that can access a shared memory subsystem 502. The system incorporates a plurality of programmable hardware memory algorithm processors (MAPs) 503a-f in the memory subsystem 502. Each MAP 503a-f can comprise a memory 504a-f and one or more field programmable gate arrays (FPGAs) 505a-f. The MAP provides a configurable functional unit and particular algorithms or portions of algorithms can be provided to the FPGAs 505a-f for processing in close coordination with a respective processor. In this example, each MAP is globally accessible by all of the processors for these purposes. In one configuration, each MAP can use Direct Memory Access (DMA) to access an associated memory 504a-f, allowing it to execute tasks independently of, and asynchronously from, the respective microprocessor 501a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 5, system on chips (SOCs), application specific integrated circuits (ASICs), or other processing and logic elements. For example, the Set Processor and Optimizer can be implemented with hardware acceleration through the use of a hardware accelerator card, such as accelerator card 312 illustrated in FIG. 3.

In some embodiments, the quality control analysis described herein was performed on an Apple Mac Pro, 64 bit architecture, 1 TB SSD drives, 128 G RAM, dual 12 core Xeon CPU's running 3.06 GHz using the Windows 7 OS. The system described in the analyses of Examples 1-6 had an on-line storage with a dual-Gigabit Ethernet network attached storage (NAS). Internet security for the system described in the analyses of examples 1-6 was provided by Oracle 9i.

Figure 6:
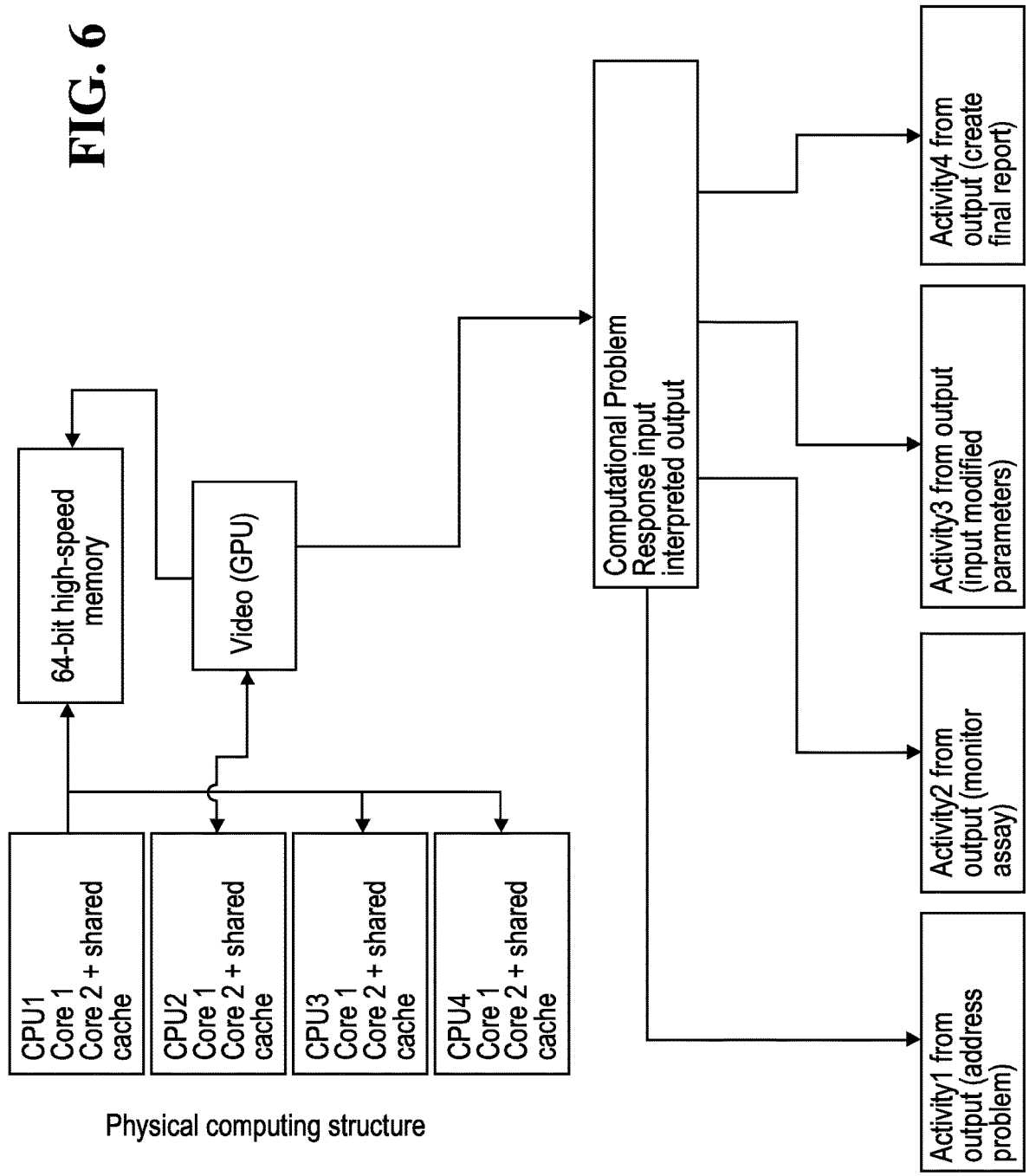
FIG. 6 is a diagram of a 1-box computer farm capable of integrating with the present invention, ideally supporting all computer needs in a single tuned system.

FIG. 6 is a diagram of single-machine parallel problem solving (multi-core, multi-CPU problem solving). Illustrated here is a diagram of commercially available one-box compute-farm (i.e. Apple Pro). Medium-speed clock coupled with full 64-bit wide memory access, high-speed L1 and L2 cache, integrated parallel GPU processors, and solid-state storage mean a tuned system with no bottlenecks. This diagram represents a model system capable of coupling to current disclosed invention.

Example 7: A Method of Quality Control

Frequently, immunosignature assays are performed in large batches of several hundred assays at a time. A general feature of immunosignatures is that the effect of the disease is limited to a relatively small number of peptides on the surface. Therefore most peptides behave similarly in any two arrays, regardless of the health status of the patient. Because of this, one can compare individual array-based assays in large batches for consistency. Assays that give substantially different overall results from the others are rerun. It is frequently necessary to consider at least two types of correlations between assay results in determining assay quality.

One is the correspondence of binding to specific peptide features between arrays. In other words, most features will bind with about the same relative intensity on one array as they would on another. This aspect can be tested with, for example, a Pearson Correlation. However, typically a Pearson Correlation does not provide a complete picture because such correlations are strongly weighted by the correspondence between the majority of peptide features. The quality of an immunosignature is strongly dictated by the high and low binding peptide features which dictate the shape of the binding distribution (the histogram of numbers of features that have a certain intensity). This distribution does not consider the peptide-to-peptide correlation, just the binding properties and dynamic range of the entire data set. The shape of the distribution can be compared between arrays by using any of a number of methods, one of which is a Kolmogorov-Smirnov test which returns a p-value (a probability value based on the likelihood that they two distributions only differed due to random statistical error).

Figure 7:
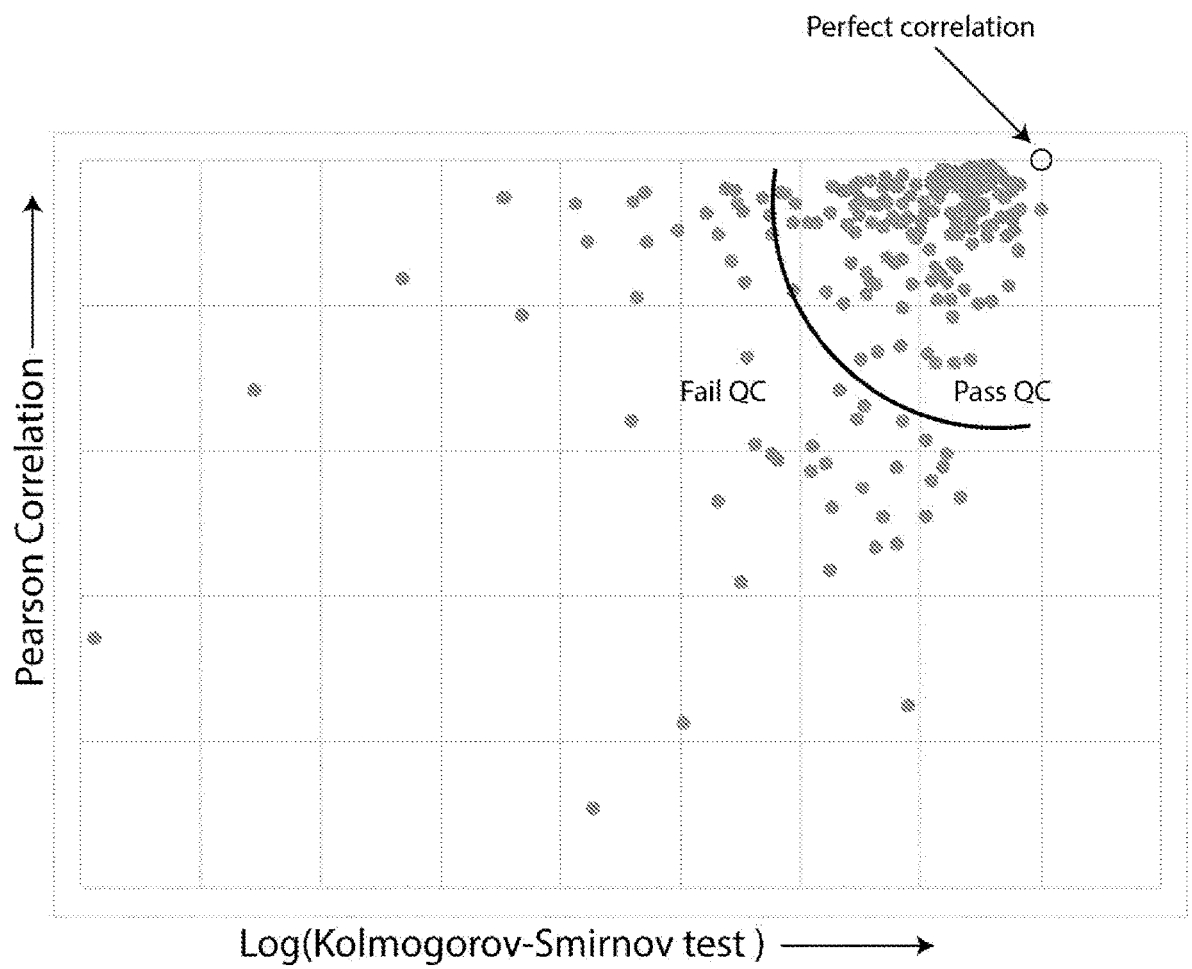
FIG. 7 is a statistical correlation utilized in a quality control analysis.

Both the Pearson Correlation and the Kolmogorov-Smirnov test approach 1.0 when the assays are similar to one another. By comparing all assays to all other assays in a batch using these two tests, one can easily determine which assays meet both criteria. FIG. 7 shows such an analysis graphically. The Y-axis is the average Pearson Correlation (the average of each array against all others is plotted). An array agrees better with other arrays the larger this value is. The X-axis is the Kolmogorov-Smirnov test (the average of the log of the p-value obtained from this test for each array against all others is plotted). Again, an array agrees better with other arrays the larger this value is. In this graph the actual values shown are simply normalized to fill the screen for viewing purposes, so only the relative values are meaningful. Also shown is a cutoff that corresponds to a particular distance defined by the two orthogonal parameters (i.e. the distance is the square root of the sum of the squares of the two values and is relative to the upper right of the graph where arrays would be in perfect agreement). The value of the cutoff used, depends on the kind of dataset involved. Assays that are either below or to the left of the line are rerun.

What is claimed is:

1. A method for determining quality and fidelity of an in situ synthesized peptide array configured for use in an immunosignature assay, comprising:
    obtaining a first binding pattern of the in situ synthesized peptide array, wherein the first binding pattern is obtained from binding with a first sample, the first sample comprising a biological sample from a subject, wherein the in situ synthesized peptide array comprises at least 100 compounds;
    obtaining a second binding pattern of an in situ synthesized reference peptide array;
    comparing the first binding pattern with the second binding pattern and calculating a correlation value, wherein the comparing comprises a direct peptide-by-peptide comparison between the first and the second binding patterns to evaluate a number of peptides expressing different patterns and a comparison between a binding profile of the first binding pattern and a binding profile of the second binding pattern to evaluate a level of similarity between the binding profiles, wherein each of the binding profiles comprises a distribution of signals measured from a population of at least 2 arrayed compounds; and
    thereby establishing synthesis quality and fidelity of the in situ synthesized peptide array, wherein a correlation value of less than a threshold level indicates a quality of an immunosignature assay using the in situ synthesized peptide array.

2. The method of claim 1, wherein the correlation value is obtained by Kolmogorov-Smirnov test, Pearson Correlation or Pearson Squared.

3. The method of claim 1, wherein the threshold level is defined as a percentage of the correlation coefficient between assays.

4. The method of claim 1, wherein the peptide array is a random or partially random peptide array.

5. The method of claim 1, wherein the first binding pattern is obtained from a subset of peptides on the peptide array, and the second binding pattern is obtained from a corresponding subset of peptides on the peptide reference array.

6. The method of claim 1, wherein the first binding pattern is obtained from binding with the first sample, the second binding pattern is obtained from binding with a second sample, wherein the first sample and the second sample are from a same species.

7. The method of claim 6, wherein the first sample and the second sample are not from the same subject.

8. The method of claim 6, wherein the species is human being.

9. The method of claim 6, wherein the first sample and the second sample are acquired from a blood sample.

10. The method of claim 1, wherein the biological sample is a blood sample, a serum sample, a plasma sample, a urine sample, a sputum sample, a mucosal sample, a peritoneal fluid sample, a tissue sample, an exudate or an effusion.

11. A method for determining quality and fidelity of an in situ synthesized peptide array configured for use in an immunosignature assay, comprising:
    providing an array of peptides, wherein the peptides are synthesized in situ in a stepwise manner on the surface of an array, wherein the in situ synthesized peptide array comprises at least 100 compounds;
    incubating a biological sample on the peptide array;
    obtaining a first binding pattern of the biological sample binding to the in situ synthesized peptide array;
    obtaining a second binding pattern of an in situ synthesized reference peptide array;
    comparing the first binding pattern with the second binding pattern and calculating a correlation value, wherein the comparing comprises a direct peptide-by-peptide comparison between the first and the second binding patterns to evaluate a number of peptides expressing different patterns and a comparison between a binding profile of the first binding pattern and a binding profile of the second binding pattern to evaluate a level of similarity between the binding profiles, wherein each of the binding profiles comprises a distribution of signals measured from a population of at least 2 arrayed compounds; and
    thereby establishing synthesis quality and fidelity of the in situ synthesized peptide array, wherein a correlation value of less than a threshold level indicates a quality of an immunosignature assay using the in situ synthesized peptide array.

12. The method of claim 11, wherein the correlation value is obtained by Kolmogorov-Smirnov test, Pearson Correlation or Pearson Squared.

13. The method of claim 11, wherein the threshold level is defined as a percentage of the correlation coefficient between assays.

14. The method of claim 11, wherein the peptide array is a random or partially random peptide array.

15. The method of claim 11, wherein the first binding pattern is obtained from a subset of peptides on the peptide array, and the second binding pattern is obtained from a corresponding subset of peptides on the peptide reference array.

16. The method of claim 11, wherein the first binding pattern is obtained from binding with the first sample, the second binding pattern is obtained from binding with a second sample, wherein the first sample and the second sample are from a same species.

17. The method of claim 16, wherein the first sample and the second sample are not from the same subject.

18. The method of claim 16, wherein the species is human being.

19. The method of claim 16, wherein the first sample and the second sample are acquired from a blood sample.

20. The method of claim 1, wherein the biological sample is a blood sample, a serum sample, a plasma sample, a urine sample, a sputum sample, a mucosal sample, a peritoneal fluid sample, a tissue sample, an exudate or an effusion.

* * * * *